US012100490B1

(12) United States Patent
Paris, III

(10) Patent No.: US 12,100,490 B1
(45) Date of Patent: *Sep. 24, 2024

(54) DE-IDENTIFYING MEDICAL HISTORY INFORMATION FOR MEDICAL UNDERWRITING

(71) Applicant: Vigilytics LLC, Victor, NY (US)

(72) Inventor: Andrew L. Paris, III, Victor, NY (US)

(73) Assignee: Vigilytics LLC, Victor, NY (US)

( * ) Notice: Subject to any disclaimer, the term of this patent is extended or adjusted under 35 U.S.C. 154(b) by 213 days.

This patent is subject to a terminal disclaimer.

(21) Appl. No.: 17/060,558

(22) Filed: Oct. 1, 2020

Related U.S. Application Data

(63) Continuation of application No. 16/131,094, filed on Sep. 14, 2018, now Pat. No. 10,886,012, which is a continuation of application No. 14/732,358, filed on Jun. 5, 2015, now Pat. No. 10,109,375, which is a continuation of application No. 12/827,745, filed on Jun. 30, 2010, now Pat. No. 9,118,641.

(60) Provisional application No. 61/222,428, filed on Jul. 1, 2009.

(51) Int. Cl.
  *H04L 29/06* (2006.01)
  *G16H 10/60* (2018.01)

(52) U.S. Cl.
  CPC ................... *G16H 10/60* (2018.01)

(58) Field of Classification Search
  CPC ...................................................... G16H 10/60
  USPC .......................................................... 713/168
  See application file for complete search history.

(56) References Cited

U.S. PATENT DOCUMENTS

| | | |
|---|---|---|
| 5,721,777 A | 2/1998 | Blaze |
| 5,956,400 A | 9/1999 | Chaum |
| 6,302,844 B1 | 10/2001 | Walker |
| 6,732,113 B1 | 5/2004 | Ober et al. |
| 6,804,787 B2 | 10/2004 | Dick |
| 6,874,085 B1 | 3/2005 | Koo |
| 6,947,561 B1 | 9/2005 | Faber |
| 7,376,667 B2 | 5/2008 | Farkkilae |
| 7,519,591 B2 | 4/2009 | Landi et al. |
| 7,650,628 B2 | 1/2010 | Zimmerman |
| 7,716,487 B2 | 5/2010 | Venkatesan |
| 7,823,207 B2 | 10/2010 | Evenhaim |

(Continued)

FOREIGN PATENT DOCUMENTS

| | | |
|---|---|---|
| CA | 2760773 | 11/2010 |
| WO | WO 2001/018631 | 3/2001 |

(Continued)

OTHER PUBLICATIONS

"Group," The American Heritage Dictionary, 2014 Houghton Mifflin Harcourt, Retrieved online: https://ahdictionary.com/word/search.html?q=group (accessed Oct. 23, 2014), 3 pages.

(Continued)

*Primary Examiner* — Evans Desrosiers
(74) *Attorney, Agent, or Firm* — Fish & Richardson P.C.

(57) ABSTRACT

A computer-implemented method includes producing information that characterizes a group of individuals from a set of private data representing characteristics of the individuals. The identity of the individuals is unattainable from the produced information. The method also includes providing the produced information to report the characteristics of the group.

18 Claims, 7 Drawing Sheets

(56) References Cited

U.S. PATENT DOCUMENTS

| | | | |
|---|---|---|---|
| 7,865,376 B2 | 1/2011 | Ober et al. |
| 7,900,245 B1 | 3/2011 | Geddes |
| 7,917,525 B2 | 3/2011 | Rawlings et al. |
| 8,037,052 B2 | 10/2011 | Kariathungal |
| 8,055,910 B2 | 11/2011 | Kocher |
| 8,108,355 B2 | 1/2012 | Zhang |
| 8,126,734 B2 | 2/2012 | Dicks et al. |
| 8,131,566 B2 | 3/2012 | Dicks et al. |
| 8,131,646 B2 | 3/2012 | Kocher |
| 8,229,742 B2 | 7/2012 | Zimmerman |
| 8,296,341 B2 | 10/2012 | Hagan |
| 8,473,452 B1 | 6/2013 | Ober et al. |
| 8,700,649 B2 | 4/2014 | Rawlings et al. |
| 8,930,404 B2 | 1/2015 | Ober et al. |
| 9,118,641 B1 | 8/2015 | Paris, III |
| 9,141,758 B2 | 9/2015 | Kress et al. |
| 9,323,892 B1 | 4/2016 | Paris, III |
| 9,355,273 B2 | 5/2016 | Stevens et al. |
| 9,633,223 B1 | 4/2017 | Blackwell et al. |
| 9,665,685 B1 | 5/2017 | Paris, III |
| 9,886,558 B2 | 2/2018 | Ober et al. |
| 9,965,651 B1 | 5/2018 | Paris, III |
| 10,109,375 B1 | 10/2018 | Paris, III |
| 10,886,012 B1 | 1/2021 | Paris, III |
| 10,943,028 B1 | 3/2021 | Paris, III |
| 2002/0016923 A1 | 2/2002 | Knaus |
| 2002/0111833 A1 | 8/2002 | Dick |
| 2002/0188869 A1 | 12/2002 | Patrick |
| 2003/0154405 A1 | 8/2003 | Harrison |
| 2004/0064341 A1 | 4/2004 | Langan et al. |
| 2004/0078236 A1 | 4/2004 | Stoodley |
| 2004/0143403 A1 | 7/2004 | Brandon et al. |
| 2004/0215981 A1 | 10/2004 | Ricciardi et al. |
| 2005/0114334 A1 | 5/2005 | Ober et al. |
| 2005/0119941 A1 | 6/2005 | James |
| 2005/0177050 A1 | 8/2005 | Cohen |
| 2005/0234739 A1 | 10/2005 | Schoenberg |
| 2005/0261941 A1 | 11/2005 | Scarlat |
| 2005/0267782 A1 | 12/2005 | Zahlmann |
| 2006/0004772 A1 | 1/2006 | Hagan et al. |
| 2006/0020611 A1 | 1/2006 | Gilbert et al. |
| 2006/0080145 A1 | 4/2006 | Cook et al. |
| 2006/0089857 A1 | 4/2006 | Zimmerman |
| 2006/0173716 A1 | 8/2006 | Wang |
| 2006/0184524 A1 | 8/2006 | Pollanz |
| 2006/0229919 A1* | 10/2006 | Pugh .............. G16H 10/65 705/3 |
| 2007/0033419 A1 | 2/2007 | Kocher |
| 2007/0043594 A1 | 2/2007 | Lavergne |
| 2007/0106752 A1 | 5/2007 | Moore |
| 2007/0106753 A1 | 5/2007 | Moore |
| 2007/0130465 A1 | 6/2007 | Zeng |
| 2007/0136237 A1 | 6/2007 | Barker et al. |
| 2007/0157297 A1 | 7/2007 | Patrick |
| 2007/0185737 A1 | 8/2007 | Friedlander |
| 2007/0192139 A1 | 8/2007 | Cookson et al. |
| 2007/0192140 A1 | 8/2007 | Gropper |
| 2007/0219824 A1 | 9/2007 | Rawlings et al. |
| 2007/0282796 A1 | 12/2007 | Evenhaim |
| 2007/0294111 A1 | 12/2007 | Settimi |
| 2008/0010254 A1 | 1/2008 | Settimi |
| 2008/0040151 A1 | 2/2008 | Moore |
| 2008/0071577 A1 | 3/2008 | Highley |
| 2008/0091474 A1 | 4/2008 | Ober et al. |
| 2008/0097914 A1 | 4/2008 | Dicks et al. |
| 2008/0103554 A1 | 5/2008 | Dicks et al. |
| 2008/0120296 A1 | 5/2008 | Kariathungal et al. |
| 2008/0133273 A1 | 6/2008 | Marshall |
| 2008/0137848 A1 | 6/2008 | Kocher |
| 2008/0147554 A1 | 6/2008 | Stevens et al. |
| 2008/0201174 A1 | 8/2008 | Ramasubramanian et al. |
| 2008/0281631 A1 | 11/2008 | Syth |
| 2008/0304663 A1 | 12/2008 | Canarad |
| 2008/0306872 A1 | 12/2008 | Felsher |
| 2008/0306952 A1 | 12/2008 | Lynn |
| 2009/0024416 A1* | 1/2009 | McLaughlin .......... G16H 10/65 705/2 |
| 2009/0070146 A1 | 3/2009 | Haider et al. |
| 2009/0112769 A1 | 4/2009 | Dicks |
| 2009/0150362 A1 | 6/2009 | Evenhaim |
| 2009/0171692 A1 | 7/2009 | Zilberman |
| 2009/0257586 A1 | 10/2009 | Takahashi |
| 2009/0287502 A1 | 11/2009 | Roberts et al. |
| 2010/0034376 A1 | 2/2010 | Okuizumi et al. |
| 2010/0114607 A1 | 5/2010 | Kress et al. |
| 2010/0162355 A1 | 6/2010 | Zimmerman et al. |
| 2010/0217973 A1 | 8/2010 | Kress |
| 2010/0287190 A1 | 11/2010 | Anderson |
| 2010/0325148 A1 | 12/2010 | Anderson |
| 2011/0077973 A1 | 3/2011 | Breitenstein et al. |
| 2011/0184748 A1 | 7/2011 | Fierro et al. |
| 2011/0191767 A1 | 8/2011 | Pinsky |
| 2011/0191822 A1 | 8/2011 | Pinsky |
| 2011/0196704 A1 | 8/2011 | Mansour |
| 2011/0225007 A1 | 9/2011 | Theis |
| 2011/0231422 A1 | 9/2011 | Rawlings |
| 2011/0255690 A1 | 10/2011 | Kocher |
| 2011/0258000 A1 | 10/2011 | Green et al. |
| 2012/0246661 A1 | 9/2012 | Nishimura |
| 2013/0246334 A1 | 9/2013 | Ahuja |
| 2014/0040308 A1 | 2/2014 | Ober et al, |
| 2014/0053252 A1 | 2/2014 | Kelsey |
| 2014/0108038 A1 | 4/2014 | Lipsky et al. |
| 2015/0046192 A1 | 2/2015 | Raduchel |
| 2015/0112973 A1 | 4/2015 | Ober et al. |
| 2016/0314248 A1 | 10/2016 | Klocek et al. |
| 2017/0316530 A1 | 11/2017 | Kress et al. |
| 2021/0182428 A1 | 6/2021 | Paris, III |

FOREIGN PATENT DOCUMENTS

| | | |
|---|---|---|
| WO | WO 2004/031922 | 4/2004 |
| WO | WO 2007/108814 | 9/2007 |
| WO | WO 2010/129653 | 11/2010 |

OTHER PUBLICATIONS

"Health Information Privacy: Business Associates," U.S. Department of Health and Human Services, Apr. 3, 2003, Retrieved online: http://www.hhs.gov/ocr/privacy/hipaa/understanding/coveredentities/businessassociates.html, (accessed Oct. 9, 2014), 2 pages.

Claerhout et al., "Privacy protection for clinical and genomic data. The use of privacy-enhancing techniques in medicine," Int. J. Med. Informatics, Mar. 2005, 74:257-265.

Eman et al., "Protecting Privacy Using k-Anonymity," J Am Med Inform Assoc., Sep. 2008, 15:627- 637.

Federal Register, "Department of Health and Human Services, 45 CFR Parts 160 and 164 Standards for Privacy of Individually Identifiable Health Information; Final Rule," National Archives and Records Administration, Dec. 28, 2000, 419 pages.

Group Insurance, 5th ed., ACTEX Publications, Jan. 2007, Chapter 28: Health Risk Adjustment, 29 pages.

Malin et al., "An Evaluation of the Current State of Genomic Data Privacy Protection Technology and a Roadmap for the Future," J. Am. Med. Inform. Assoc., Jan. 2005, 12:28-34.

*Milliman, Inc., et al.* Plaintiff v. *Gradient A.I. Corp., et al.*, Defendant, United States District Court for the District of Massachusetts, Civil Action No. 1:21-CV-10865-NMG, Summons in a Civil Action, filed May 25, 2021, 2 pages (case 1:21-cv-10865-NMG, D6).

*Milliman, Inc., et al.* Plaintiff v. *Gradient A.I. Corp., et al.*, Defendant, United States District Court for the District of Massachusetts, Civil Action No. 1:21-CV-10865-NMG, Summons in a Civil Action, filed May 26, 2021, 2 pages (case 1:21-cv-10865-NMG, D9).

*Milliman, Inc., et al.*, Plaintiff v. *Gradient A.I. Corp., et al.*, Defendants. Memorandum & Order, filed on Jan. 19, 2023, 13 pages (Civil Action No. 21-10865-NMG, D133).

*Milliman, Inc., et al.*, Plaintiff v. *Gradient A.I. Corp., et al.*, Defendants. Memorandum & Order, filed on Jan. 19, 2023, 17 pages (Civil Action No. 21-10865-NMG, D134).

(56) References Cited

OTHER PUBLICATIONS

*Milliman, Inc., et al.*, Plaintiff v. *Gradient A.I. Corp., et al.*, Defendants. United States District Court District of Massachusetts, Memorandum and Order on Motion to Compel and Cross Motion for Protective Order (##54, 59), filed Jul. 11, 2022, 6 pages (case 1:21-cv-10865-NMG, D70).
*Milliman, Inc., et al.*, Plaintiffs, v. *Gradient A.I. Corp., et al.*, Defendants. United States District Court District of Massachusetts, Order, Filed on Apr. 7, 2022, 3 pages (case 1:21-cv-10865-NMG, D52).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. [Proposed] Order Granting Plaintiff Vigilytics LLC's Unopposed Motion to Withdraw Joseph Dorris as Counsel, filed on Apr. 3, 2023, 1 page (Case 1:21-cv-10865-NMG, D142-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Affidavit of Kevin C. Quigley in Support of Defendant Gradient'S Responsive Claim Construction Brief, filed on Dec. 8, 2022, 3 pages (case 1:21-cv-10865-NMG, DI29).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Certificate of Attorney Ashley A. Bolt, filed Apr. 3, 2023, 2 pages (Case 1:21-cv-10865-NMG, D141-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Declaration of Mark G. Knedeisen in Support of Plaintiffs' Responsive Claim Construction Brief, Exhibit A, filed on Dec. 8, 2022, 216 pages (Case 1:21-cv-10865-NMG, D127-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Declaration of Mark G. Knedeisen in Support of Plaintiffs' Responsive Claim Construction Brief, filed on Dec. 8, 2022, 1 page (Case 1:21-cv-10865, D127).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendant Gradient's Responsive Claim Construction Brief, filed on Dec. 8, 2022, 24 pages (case 1:21-cv-10865-NMG, D128).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Motion for Reconsideration of Order Denying Summary Judgment on Milliman's Trade Secret Claims, filed May 18, 2023, 1 page (Case Case 1:21-cv-10865-NMG, D151).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Memorandum in Support of Motion for Reconsideration of Order Denying Summary Judgment on Milliman's Trade Secret Claims, Filed on Feb. 10, 2023, 10 pages (Civil Action No. 1:21-cv-10865-NMG, D136).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Motion for Reconsideration of Order Denying Summary Judgment on Milliman's Trade Secret Claims, Filed on Feb. 10, 2023, 2 pages (Civil Action No. 1:21-cv-10865-NMG, D135).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, dated Aug. 25, 2022, 65 pages (case 1:21-cv-10865-NMG).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 1-A: Preliminary Invalidity Contentions for U.S. Pat. No. 9,118,641 dated Aug. 25, 2022, 30 pages (case 1:21-cv-10865-NMG, 1-A).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 1-B: Preliminary Invalidity Contentions for U.S. Pat. No. 9,118,641, dated Aug. 25, 2022, 3 8 pages (case 1:21-cv-10865-NMG, 1-B).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 1-C: Preliminary Invalidity Contentions for U.S. Pat. No. 9,118,641, dated Aug. 25, 2022, 43 pages (case 1:21-cv-10865-NMG, 1-C).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 1-D: Preliminary Invalidity Contentions for U.S. Pat. No. 9,118,641, dated Aug. 25, 2022, 42 pages (Case 1:21-cv-10865-NMG, 1-D).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 2-A: Preliminary Invalidity Contentions for U.S. Pat. No. 10,109,375, dated Aug. 25, 2022, 21 pages (Case 1:21-cv-10865-NMG, 2-A).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 2-B: Preliminary Invalidity Contentions for U.S. Pat. No. 10,109,375, dated Aug. 25, 2022, 27 pages (Case 1:21-cv-10865-NMG, 2-B).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 2-C: Preliminary Invalidity Contentions for U.S. Pat. No. 10,109,375, dated Aug. 25, 2022, 31 pages (Case 1:21-cv-10865-NMG, 2-C).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 2-D: Preliminary Invalidity Contentions for U.S. Pat. No. 10,109,375, dated Aug. 25, 2022, 30 pages (Case 1:21-cv-10865-NMG, 2-D).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 3-A: Preliminary Invalidity Contentions for U.S. Pat. No. 10,886,012, dated Aug. 25, 2022, 17 pages (Case 1:21-cv-10865-NMG, 3-A).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 3-B: Preliminary Invalidity Contentions for U.S. Pat. No. 10,886,012. dated Aug. 25, 2022, 22 pages (Case 1:21-cv-10865-NMG, 3-B).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 3-C: Preliminary Invalidity Contentions for U.S. Pat. No. 10,886,012, dated Aug. 25, 2022, 26 pages (Case 1:21-cv-10865-NMG, 3-C).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 3-D: Preliminary Invalidity Contentions for U.S. Pat. No. 10,886,012, dated Aug. 25, 2022, 25 pages (Case 1:21-cv-10865-NMG, 3-D).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 4-A: Preliminary Invalidity Contentions for U.S. Pat. No. 9,323,892, dated Aug. 25, 2022, 17 pages (Case 1:21-cv-10865-NMG, 4-A).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Conten-

(56) References Cited

OTHER PUBLICATIONS tions, Exhibit 4-B: Preliminary Invalidity Contentions for U.S. Pat. No. 9,323,892, dated Aug. 25, 2022, 19 pages (Case 1:21-cv-10865-NMG, 4-B).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 4-C: Preliminary Invalidity Contentions for U.S. Pat. No. 9,323,892, dated Aug. 25, 2022, 23 pages (Case 1:21-cv-10865-NMG, 4-C).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 4-D: Preliminary Invalidity Contentions for U.S. Pat. No. 9,323,892, dated Aug. 25, 2022, 14 pages (Case 1:21-cv-10865-NMG, 4-D).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 5-A: Preliminary Invalidity Contentions for U.S. Pat. No. 9,665,685, dated Aug. 25, 2022, 25 pages (Case 1:21-cv-10865-NMG, 5-A).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 5-B: Preliminary Invalidity Contentions for U.S. Pat. No. 9,665,685, dated Aug. 25, 2022, 38 pages (Case 1:21-cv-10865-NMG, 5-B).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 5-C: Preliminary Invalidity Contentions for U.S. Pat. No. 9,665,685, dated Aug. 25, 2022, 42 pages (Case 1:21-cv-10865-NMG, 5-C).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 5-D: Preliminary Invalidity Contentions for U.S. Pat. No. 9,665,685, dated Aug. 25, 2022, 42 pages (Case 1:21-cv-10865-NMG, 5-D).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 6-A: Preliminary Invalidity Contentions for U.S. Pat. No. 9,965,651, dated Aug. 25, 2022, 30 pages (Case 1:21-cv-10865-NMG, 6-A).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 6-B: Preliminary Invalidity Contentions for U.S. Pat. No. 9,965,651, dated Aug. 25, 2022, 42 pages (Case 1:21-cv-10865-NMG, 6-B).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 6-C: Preliminary Invalidity Contentions for U.S. Pat. No. 9,965,651, dated Aug. 25, 2022, 46 pages (Case 1:21-cv-10865-NMG, 6-C).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Invalidity Contentions, Exhibit 6-D: Preliminary Invalidity Contentions for U.S. Pat. No. 9,965,651, dated Aug. 22, 2022, 46 pages (Case 1:21-cv-10865-NMG, 6-D).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Noninfringement Contentions, Exhibit 1: Preliminary Non-Infringement Contentions for U.S. Pat. No. 9,118,641, dated Aug. 25, 2022, 2 pages (Case 1:21-cv-10865-NMG, Exhibit 1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Noninfringement Contentions, Exhibit 2: Preliminary Non-Infringement Contentions for U.S. Pat. No. 10,109,375, dated Aug. 25, 2022, 2 pages (Case 1:21-cv-10865-NMG, Exhibit 2).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Noninfringement Contentions, Exhibit 3: Preliminary Non-Infringement Contentions for U.S. Pat. No. 10,886,012, dated Aug. 25, 2022, 1 page (Case 1:21-cv-10865-NMG, Exhibit 3).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Noninfringement Contentions, Exhibit 4: Preliminary Non-Infringement Contentions for U.S. Pat. No. 9,323,892, dated Aug. 25, 2022, 2 pages (Case 1:21-cv-10865-NMG, Exhibit 4).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Noninfringement Contentions, Exhibit 5: Preliminary Non-Infringement Contentions for U.S. Pat. No. 9,665,685, dated Aug. 25, 2022, 2 pages (Case 1:21-cv-10865-NMG, Exhibit 5).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Noninfringement Contentions, Exhibit 6: Preliminary Non-Infringement Contentions for U.S. Pat. No. 9,965,651, dated Aug. 25, 2022, 2 pages (Case 1:21-cv-10865-NMG, Exhibit 6).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Preliminary Non-Infringement Contentions, filed on Aug. 25, 2022, 6 pages (Case 1:21-cv-10865-NMG).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Reply in Support of Motion for Reconsideration of Order Denying Summary Judgment on Milliman'S Trade Secret Claims, filed Mar. 7, 2023, 5 pages (Case Civil Action No. 1:21-cv-10865-NMG, D140).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Reply in Support of Motion for Reconsideration of Order Denying Summary Judgment on Milliman'S Trade Secret Claims, filed on Mar. 7, 2023, 5 pages (case 1:21-cv-10865-NMG, D140).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Defendants' Unopposed Request for Leave To File Reply Brief and Request for Oral Argument, filed on Feb. 28, 2023, 2 pages (Civil Action No. 1:21-cv-10865-NMG, D138).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Exhibit 5, Deposition of Aviel D. Rubin, Ph D., filed on Dec. 8, 2022, 86 pages (case 1:21-cv-10865-NMG, 129-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Exhibit 6, Plaintiffs' Disclosure of Claim Terms and Proposed Preliminary Constructions, filed on Dec. 8, 2022, 6 pages (case 1:21-cv-10865-NMG, 129-2).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Exhibit 7, Defendants' List of Claim Terms to Be Construed and Their Proposed Constructions, filed on Dec. 8, 2022, 8 pages (case 1:21-cv-10865-NMG, D129-3).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. Exhibit A, [Proposed] Order Granting Joint Motion to Modify Scheduling Order, filed Apr. 17, 2023, 2 pages (Case 1:21-cv-10865-NMG, D146-1).

*Milliman, Inc., Milliman Solutions, LLC, and Vigilytics LLC*, Plaintiffs, vs. *Gradient A.I. Corp., Stanford A. Smith, and Samuel Chase

(56) References Cited

OTHER PUBLICATIONS

*Pettus*, Defendants. Exhibit A, [Proposed] Order Granting Plaintiffs' Motion to Modify Scheduling Order, filed Apr. 3, 2023, 3 pages (Case 1:21-cv-10865-NMG, D144-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Ex A to Pltfs Opp to Defs Partial Mot to Dismiss for Failure to State a Claim, filed Jul. 26, 2021, 17 pages (case 21-cv-10865, D26-2).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Ex B to Pltfs Opp to Defs Partial Mot to Dismiss for Failure to State a Claim, filed Jul. 26, 2021, 2 pages (Case 21-cv-10865, D26-3).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, [Proposed] Order Establishing Protocol Governing Production of Documents and Electronically Stored Information ("ESI"), Exhibit B, filed on Mar. 25, 2022, 15 pages (Case 1:21-cv-10865-NMG, D48-2).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, [Proposed] Order On Defendants' Cross-Motion for a Protective Order, filed on May 25, 2022, 1 page (case 1:21-cv-10865-NMG, D59-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, [Proposed] Plaintiffs' Surreply in Opposition to Defendants' Partial Motion to Dismiss for Failure to State a Claim Exhibit A, filed Aug. 11, 2021, 12 pages (case Civil Action No. 21-cv-10865, D30-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, [Proposed] Protective Order, Exhibit A, filed on Mar. 25, 2022, 34 pages (Case 1:21-cv-10865-NMG, D48-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, [Proposed] Scheduling Order, Exhibit A, filed on Mar. 28, 2022, 6 pages (Case 1:21-cv-10865-NMG, D50-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, [Proposed] Scheduling Order, filed Mar. 14, 2022, 5 pages, (case 1:21-cv-10865-NMG, D44).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Affidavit of Kevin C. Quigley in Support of Defendants' Motion for Summary Judgment, filed Sep. 16, 2022, 2 pages (Case 1:21-cv-10865-NMG, D91).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Affidavit of Kevin C. Quigley in Support of Defendants' Motion for Summary Judgment, filed on Oct. 20, 2022, 2 pages (Case 1:21-cv-10865-NMG, D111).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Answer and Counterclaims of Defendants Gradient A.I. Corp., Stanford A. Smith, and Samuel Chase Pettus, filed on Mar. 25, 2022, 64 pages (case 1:21-cv-10865-NMG).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Assented-to Motion for Leave to File Reply in Support of Plain Fiffs' Motion to Compel Compliance With the Court'S Automatic Patent Disclosures, filed on Oct. 21, 2022, 4 pages (Case 1:21-cv-10865-NMG, D1113).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Asset Purchase Agreement, Exhibit A, filed Mar. 25, 2022, 27 pages (Case 1:21-cv-10865-NMG, D49-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Certification of Milliman, Inc., Milliman Solutions, LLC, and Vigilytics, LLC Pursuant to Local Rule 16.1, filed on Mar. 3, 2022, 3 pages (case 1:21-cv-10865, D42).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Combined Statement of Facts Regardingdefendants' Motion for Summary Judgment on Milliman'S Trade Secret Claims, filed on Oct. 28, 2022, 31 pages (Case 1:21-cv-10865-NMG, D119).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Dr. Aviel D. Rubin, Exhibit A, filed Sep. 16, 2022, 47 pages (case 1:21-cv-10865-NMG, D86-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Kevin C. Quigley, Exhibit 1, Filed on Oct. 20, 2022, 14 pages (Case 1:21-cv-10865-NMG, D111-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Kevin C. Quigley, Exhibit 2, filed on Oct. 20, 2022, 12 pages (Case 1:21-cv-10865-NMG, D111-2).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Kevin C. Quigley, Exhibit 3, filed on Oct. 20, 2022, 76 pages (Case 1:21-cv-10865-NMG, D111-3).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Kevin C. Quigley, Exhibit 4, filed on Oct. 20, 2022, 9 pages (Case 1:21-cv-10865-NMG, D111-4).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 3, filed on Oct. 20, 2022, 20 pages (Case 1:21-cv-10865-NMG, D109-3).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 4, filed on Oct. 20, 2022, 11 pages (Case 1:21-cv-10865-NMG, D109-4).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in

(56) References Cited

OTHER PUBLICATIONS

Support of Plaintiffs' Opening Claim Construction Brief, Exhibit 5, filed on Oct. 20, 2022, 15 pages (Case 1:21-cv-10865-NMG, D109-5).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plain Tiffs' Opening Claim Construction Brief, Exhibit 6, filed on Oct. 20, 2022, 6 pages (Case 1:21-cv-10865-NMG, D109-6).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 7, filed on Oct. 20, 2022, 8 pages (Case 1:21-cv-10865-NMG, D109-7).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 8, filed on Oct. 20, 2022, 6 pages (Case 1:21-cv-10865-NMG, D109-8).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 9, filed on Oct. 20, 2022, 6 pages (Case 1:21-cv-10865-NMG, D109-9).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 10, filed on Oct. 20, 2022, 6 pages (Case 1:21-cv-10865-NMG, D109-10).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plain Tiffs' Opening Claim Construction Brief, Exhibit 11, filed on Oct. 20, 2022, 6 pages (Case 1:21-cv-10865-NMG, D109-11).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, filed on Oct. 20, 2022, 3 pages (Case 1:21-cv-10865-NMG, D109).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Declaration of Dr. Aviel D. Rubin, Exhibit 1, filed on Oct. 20, 2022, 49 pages (Case 1:21-cv-10865-NMG, D109-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Mark G. Knedeisen in Support of Plaintiffs' Opening Claim Construction Brief, Exhibit 2, filed on Oct. 20, 2022, 15 pages (Case 1:21-cv-10865-NMG, D109-2).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Noah C. Graubart in Support of Plaintiffs' Opposition To Defendants' Partial Motion to Dismiss for Failure to State a Claim, filed Jul. 26, 2021, 2 pages (case 21-cv-10865, D26-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Sophie F. Wang, Esq. in Support of Memorandum in Support of Defendants' Partial Motion To Dismiss for Failure to State a Claim, filed Jul. 7, 2021, 27 pages, (case 1:21-cv-10865-NMG, D23).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, filed Oct. 14, 2022, 10 pages (Case 1:21-cv-10865-NMG, D106).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit A, filed Oct. 14, 2022, 27 pages (Case 1:21-cv-10865-NMG, D106-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit B, filed Oct. 14, 2022, 10 pages (case 1:21-cv-10865-NMG, D106-2).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit C, filed Oct. 14, 2022, 2 pages (Case 1:21-cv-10865-NMG, D106-3).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit D, Filed on Oct. 14, 2022, 2 pages (Case 1:21-cv-10865-NMG, DI06-4).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit E, filed on Oct. 14, 2022, 2 pages (Case 1:21-cv-10865-NMG, D106-5).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit F, filed on Oct. 14, 2022, 2 pages (Case 1:21-cv-10865-NMG, D106-6).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit G, filed on Oct. 14, 2022, 2 pages (Case 1:21-cv-10865-NMG, DI06-7).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit H, filed on Oct. 14, 2022, 2 pages (Case 1:21-cv-10865-NMG, D106-8).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit I, filed on Oct. 14, 2022, 2 page (Case 1:21-cv-10865-NMG, D106-9).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the

(56) References Cited

OTHER PUBLICATIONS

District of Massachusetts, Declaration of Stephen A. White, Exhibit J, filed on Oct. 14, 2022, 2 pages (Case 1:21-cv-10865-NMG, D106-10).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit K, filed on Oct. 14, 2022, 2 pages (Case 1:21-cv-10865-NMG, D106-11).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit L, filed on Oct. 14, 2022, 2 pages (Case 1:21-cv-10865-NMG, D106-12).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Declaration of Stephen A. White, Exhibit M, filed on Oct. 1, 2022, 2 pages (Case 1:21-cv-10865-NMG, D106-13).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendant Gradient A.I. Corp.'s Corporate Disclosure Statement, filed Jul. 7, 2021, 2 pages (case 1:21-cv-10865-NMG, D20).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendant Gradient's Opening Claim Construction Brief, filed on Oct. 20, 2022, 24 pages (Case 1:21-cv-10865-NMG, D110).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Motion for Extension of Time to Answer or Respond to Complaint, filed Jun. 16, 2021, 1 page (case 1:21-cv-10865-NMG, D15).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Assented-To Motion for Leave to File a Reply Brief in Support of Defendants' Partial Motion to Dismiss for Failure to State a Claim, filed Aug. 3, 2021, 3 pages (Civil Action No. 1:21-cv-10865-NMG, D27).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Assented-to Motion for Leave to File Under Seal, filed on Aug. 25, 2022, (case 1:21-cv-10865-NMG, D76).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Assented-to Motion for Leave to File Under Seal, filed on Sep. 16, 2022, 2 pages (Case 1:21-cv-10865-NMG, D92).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Assented-to Motion for Leave to File Under Seal, Filed Sep. 30, 2022, 2 pages (Case 1:21-cv-10865-NMG, D100).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Cross-Motion for a Protective Order, filed on May 25, 2022, 3 pages (Case 1:21-cv-10865-NMG, D59).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Local Rule 16.1(D)(3) Certification, filed on Mar. 3, 2022, 2 pages (Case 1:21-cv-10865-NMG, D40).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Memorandum in Support of Summary Judgment on Milliman's Trade Secret Claims, filed Sep. 16, 2022, 21 pages, (case 1:21-cv-10865-NMG, D89).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Motion for Extension of Time to Answer or Respond to Complaint, filed Jun. 16, 2021, 7 pages (case 1:21-cv-10865-NMG, D13).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Motion for Summary Judgment on Milliman's Trade Secret Claims (Counts VII-XII), filed on Sep. 16, 2022, 2 pages (case 1:21-cv-10865-NMG, D88).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Partial Motion to Dismiss for Failure to State a Claim, filed Jul. 7, 2021, 2 pages (1:21-cv-10865-NMG, D21).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Preliminary Non-Infringement Contentions, Exhibit H, filed Sep. 16, 2022, 18 pages (Case 1:21-cv-10865-NMG, D86-8).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Reply in Support of Summary Judgment, filed on Oct. 28, 2022, 9 pages (Case 1:21-cv-10865-NMG,D118).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Request for Leave to File Summary Judgment Reply, filed on Oct. 20, 2022, 2 pages (Case 1:21-cv-10865-NMG, DI07).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Responses and Objections to Plaintiffs' First Set of Interrogatories to Defendants, Exhibit D, filed on May 11, 2022, 21 pages (Case 1:21-cv-10865-NMG, D55-4).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Responses and Objections to Plaintiffs' First Set of Requests for Production of Documents and Things to Defendants, Exhibit E, filed on May 11, 2022, 50 pages (Case 1:21-cv-10865-NMG, D55-5).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Defendants' Statement of Undisputed Material Facts Supporting Summary Judgment on Milliman's Trade Secret Claims, filed Sep. 16, 2022, 8 pages (case 1:21-cv-10865-NMG, D90).
*Milliman, Inc., Milliman Solutions, LLC, and Vigilytics LLC*, Plaintiffs, vs. *Gradient A.I. Corp., Stanford A. Smith, and Samuel Chase

(56) References Cited

OTHER PUBLICATIONS

*Pettus*, Defendants. In the United States District Court for the District of Massachusetts, Exhibit A, United States Court of Appeals for the Federal Circuit, Personalweb Technologies LLC, Plaintiff-Appellant, Google LLC, Youtube, LLC, Defendants-Appellees, 2020-1553, filed Aug. 24, 2021, 17 pages (case Civil Action No. 1:21-cv-10865-NMG, D33-1).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Exhibit B, filed Mar. 25, 2022, 7 pages (case 1:21-cv-10865-NMG, D49-2).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Exhibit F, filed on May 11, 2022, 6 pages (case 1:21-cv-10865-NMG, D55-6).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Gradient's Memorandum (1) In Opposition to Milliman's Motion to Compel; And (2) In Support of Cross-Motion for Protective Order, filed on May 25, 2022, 19 pages (case 1:21-cv-10865-NMG, D60).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Gradient's Opposition to Mtlliman'S Renewed Motion to Compel, Redacted, filed Aug. 26, 2022, 9 pages (case 1:21-cv-10865-NMG, D78).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Gradient's Opposition to Plain Fiffs' L.R. 16.6 Motion to Compel, filed on Sep. 30, 2022, 8 pages (Case 1:21-cv-10865-NMG, D99).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Gradient's Supplemental Memorandum Regarding Trade Secret Identification, filed Jun. 23, 2022, 6 pages (case 1:21-cv-10865-NMG, D64).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Joint Claim Construction Statement, filed on Sep. 29, 2022, 11 pages (Case 1:21-cv-10865-NMG, D98).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Joint Motion for Entry of [Proposed] Scheduling Order, filed Mar. 28, 2022, 3 pages (Case 1:21-cv-10865-NMG, D50).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Joint Motion for Entry of Protective Order and Order Establishing Protocol Governing Production of Documents and Electronically Stored Information, filed on Mar. 25, 2022, 4 pages (case Civil Action No. 1:21-cv-10865-NMG, D48).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Joint Motion for Entry of Protective Order and Order Establishing Protocol Governing Production of Documents and Electronically Stored Information, filed on Apr. 6, 2022, 1 page (Case 1:21-cv-10865-NMG, D51).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Joint Statement, Filed on Mar. 3, 2022, 16 pages (case 1:21-cv-10865-NMG, D41).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Memorandum and Order on Motions to Compel (##71, 85), filed on Nov. 10, 2022, 8 pages (Case 1:21-cv-10865-NMG, D123).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Memorandum in Support of Defendants' Partial Motion to Dismiss for Failure to State a Claim, filed Jul. 7, 2021, 25 pages (case 1:21-cv-10865-NMG, D22).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Memorandum in Support of Plaintiffs' Motion to Compel Discovery Responses, filed on May 11, 2022, 16 pages (case 1:21-cv-10865-NMG, D55).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Memorandum in Support of Plaintiffs' Renewed Motion To Compel Discovery Responses, filed on Aug. 12, 2022, 12 pages (case 1:21-cv-10865-NMG, D72).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Memorandum in Support of Plaintiffs' Renewed Motion to Compel Discovery Responses, Exhibit E, filed on Aug. 12, 2022, (case 1:21-cv-10865-NMG, D72-5).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Motion for Admission Pro Hac Vice of Patrick J. Mcelhtnny, Mark G. Knedeisen and Anna Shabalov, filed on May 26, 2021, 8 pages (case 1:21-cv-10865-NMG, D8).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Motion for Admission Pro Hac Vice of Noah C. Graubart and Joseph R. Dorris, filed on Jun. 1, 2021, 2 pages (case 1:21-cv-10865-NMG, D11).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Notice of Appearance, filed Jul. 7, 2021, 1 page (case 1:21-cv-10865-NMG, D17).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Notice of Appearance, filed Jul. 7, 2021, 1 page (case 1:21-cv-10865-NMG, D18).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Notice of Appearance, filed Jul. 7, 2021, 1 page (case 1:21-cv-10865-NMG, D19).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Notice of Appearance, filed Mar. 14, 2022, 1 page, (case 1:21-cv-10865-NMG, D45).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Notice of Appearance, filed on Mar. 25, 2022, 1 page (case Civil Action No. 1:21-cv-10865-NMG, D47).

*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the

(56) References Cited

OTHER PUBLICATIONS

District of Massachusetts, Notice of Appearance, filed on Nov. 10, 2022, 2 pages (Case 1:21-cv-10865-NMG, D122).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Notice of Supplemental Authority in Support of Defendants' Partial Motion to Dismiss, filed Aug. 24, 2021, 3 pages (case Civil Action No. 1:21-cv-10865-NMG, D33).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Notice Regarding Timing of Defendants' Forthcoming Motion for Partial Summary Judgment, filed on Sep. 7, 2022, 1 page (Case 1:21-cv-10865-NMG, D84).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Answer to Defendants' Counterclaims, filed Apr. 15, 2022, 21 pages (case 1:21-cv-10865-NMG, D53).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Assented-to Motion for Leave to File a Surreply Brief in Opposition To Defendants' Partial Motion To Dismiss for Failure to State a Claim, filed on Aug. 11, 2021, 3 pages (Case Civil Action No. 21-cv-10865, D30).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' First Set of Interrogatories To Defendants, Exhibit B, filed on May 11, 2022, 10 pages (case 1:21-cv-10865-NMG, D55-2).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' First Set of Requests for Production of Documents and Things to Defendants, Exhibit C, filed on May 11, 2022, 17 pages (Case 1:21-cv-10865-NMG, D55-3).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Memorandum in Opposition to Defendants' Motion for Summary Judgment on Milliman's Trade Secret Claims, filed on Oct. 14, 2022, 26 pages (case 1:21-cv-10865-NMG, D104).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Memorandum in Support of Their Motion to Compel Compliance With the Court'S Automatic Patent Disclosures, filed on Sep. 16, 2022, 24 pages (Case 1:21-cv-10865-NMG, D86).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Motion to Compel Compliance With Automatic Patent Disclosures, filed Sep. 16, 2022, 4 pages (Case 1:21-cv-10865-NMG, D85).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Motion to Compel Discovery Responses, filed May 11, 2022, 4 pages (case 1:21-cv-10865-NMG, D54).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Opening Claim Construction Brief, filed on Oct. 20, 2022, 28 pages (Case 1:21-cv-10865-NMG, D108).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Opposition to Defendants' Motion for a Sixty ("60") Day Extension of Time to Answer or Respond to Complaint, Filed Jun. 16, 2021, 13 pages (case 1:21-cv-10865, D14).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Opposition to Defendants' Partial Motion to Dismiss for Failure to State a Claim, filed Jul. 26, 2021, 27 pages, (case 21-cv-10865, D26).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Opposition to Defendants' Motion for Protective Order, filed on Jun. 8, 2022, 16 pages (Case 1:21-cv-10865-NMG, D62).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Renewed Motion to Compel Discovery Responses, filed on Aug. 12, 2022, 4 pages (case 1:21-cv-10865-NMG, D71).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Reply in Support of Their Motion to Compel Compliance With the Court'S Automatic Patent Disclosures, filed on Oct. 21, 2022, 13 pages (Case 1:21-cv-10865-NMG, D113-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Reply in Support of Their Motion to Compel Compliance With the Court's Automatic Patent Disclosures, filed on Oct. 24, 2022, 13 pages (Case 1:21-cv-10865-NMG, D115).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Response To Defendants' Notice of Supplemental Authority, filed Sep. 1, 2021, 5 pages (case Civil Action No. 21-cv-10865, D34-1).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Response to Defendants' Notice of Supplemental Authority, filed Sep. 2, 2021, 5 pages (Case Civil Action No. 21-cv-10865, D36).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Response to Defendants' Statement of Allegedly Undisputed Material Facts Supporting Summary Judgment on Mtlliman's Trade Secret Claims, filed on Oct. 14, 2022, 28 pages (Case 1:21-cv-10865-NMG, D105).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Supplemental Brief Regarding Applicability of the Massachusetts Uniform Trade Secrets Act, filed on Jun. 23, 2022, 11 pages (Case 1:21-cv-10865-NMG, D65).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. In the United States District Court for the District of Massachusetts, Plaintiffs' Surreply in Opposition To

(56) References Cited

OTHER PUBLICATIONS

Defendants' Partial Motion to Dismiss for Failure to State a Claim, filed Aug. 12, 2021, 11 pages (Case Civil Action No. 21-cv-10865, D32).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Plaintiffs' Unopposed Motion for Extension of Time To Respond to Defendants' Motion to Dismiss, filed Jul. 15, 2021, 5 pages, (case 21-cv-10865-NMG, D24).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Plaintiffs' Unopposed Motion for Leave to File Response to Defendants' Notice of Supplemental Authority in Support of Their Partial Motion to Dismiss, filed Sep. 1, 2021, 4 pages, (Case 21-cv-10865, D34).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Plaintiffs' Unopposed Motion for an Order Setting a Scheduling Conference, filed on Feb. 7, 2022, 3 pages (Case Civil Action No. 21-cv-10865, D37).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Plaintiffs' Unopposed Motion for Leave to File Under Seal, filed on May 11, 2022, 4 pages (Case 1:21-cv-10865-NMG, D56).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Plaintiffs' Unopposed Motion for Leave to File Under Seal, filed Aug. 12, 2022, (case 1:21-cv-10865-NMG, D73).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Plaintiffs' Unopposed Motion for Leave to File Reply in Support of Motion To Compel, filed on Sep. 2, 2022, 4 pages (Case 1:21-cv-10865-NMG, D79).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Plaintiffs' Unopposed Motion for Leave to File Reply in Support of Motion To Compel, Exhibit A, filed on Sep. 2, 2022, 5 pages (case 1:21-cv-10865-NMG, D79-2).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Plaintiffs' Unopposed Motion for Leave To File Under Seal, filed Sep. 16, 2022, 4 pages (Case 1:21-cv-10865-NMG, D87).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Plaintiffs' Unopposed Supplemental Motion for Leave to File Under Seal, filed on Jul. 7, 2022, 4 pages (Case 1:21-cv-10865-NMG, D67).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Reply Brief in Support of Defendants' Partial Motion to Dismiss for Failure to State a Claim, filed on Aug. 4, 2021, 13 pages (case 1:21-cv-10865-NMG, D29).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Reply in Support of Plain Tiffs' Renewed Motion to Compel Discovery Responses, filed on Sep. 2, 2022, 11 pages (Case 1:21-cv-10865-NMG, D79-1).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Reply in Support of Plaintiffs' Renewed Motion to Compel Discovery Responses, filed on Sep. 6, 2022, 16 pages (Case 1:21-cv-10865-NMG, D83).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Rule 7.1 Corporate Disclosure Statement, filed on May 26, 2021, 2 pages (case 1:21-cv-10865-NMG, D7).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Rule 7.1 Corporate Disclosure Statement, filed on May 25, 2021, 2 pages (case 1:21-cv-10865-NMG, D3).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Rule 7.1 Corporate Disclosure Statement, filed on May 25, 2021, 2 pages (case 1:21-cv-10865-NMG, D4).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts,[Proposed] Reply Brief in Support of Defendants' Partial Motion To Dismiss for Failure To State a Claim, Exhibit A, filed on Aug. 3, 2021, 14 pages (Case 1:21-cv-10865-NMG, D27-1).

Milliman, Inc., Milliman Solutions, LLC, and Vigilytics LLC, Plaintiffs, vs. Gradient A.I. Corp., Stanford A. Smith, and Samuel Chase Pettus, Defendants. In the United States District Court for the District of Massachusetts, Complaint, filed May 25, 2021, 197 pages (case 1:21-cv-10865-NMG, D1).

Milliman, Inc., Milliman Solutions, LLC, and Vigilytics LLC, Plaintiffs, vs. Gradient A.I. Corp., Stanford A. Smith, and Samuel Chase Pettus, Defendants. Joint Motion to Modify Scheduling Order to Extend Discovery and Withdraw Prior Related Motion (DKT. 144), filed on Apr. 17, 2023, 7 pages (Case 1:21-cv-10865-NMG, D146).

Milliman, Inc., Milliman Solutions, LLC, and Vigilytics LLC, Plaintiffs, vs. Gradient A.I. Corp., Stanford A. Smith, and Samuel Chase Pettus, Defendants. Joint Motion To Modify Scheduling Order To Extend Discovery and Withdraw Prior Related Motion (PKT. 144), filed Apr. 21, 2023, 1 page (Case 1:21-cv-10865-NMG, D147).

Milliman, Inc., Milliman Solutions, LLC, and Vigilytics LLC, Plaintiffs, vs. Gradient A.I. Corp., Stanford A. Smith, and Samuel Chase Pettus, Defendants. Motion for Admission Pro Hac Vice of Ashley A. Bolt, filed on Apr. 3, 2023, 2 pages (Case 1:21-cv-10865-NMG, D141).

Milliman, Inc., Milliman Solutions, LLC, and Vigilytics LLC, Plaintiffs, vs. Gradient A.I. Corp., Stanford A. Smith, and Samuel Chase Pettus, Defendants. Notice of Appearance, filed on Jan. 12, 2023, 2 pages (case 1:21-cv-10865-NMG, D131).

Milliman, Inc., Milliman Solutions, LLC, and Vigilytics LLC, Plaintiffs, vs. Gradient A.I. Corp., Stanford A. Smith, and Samuel Chase Pettus, Defendants. Order Gran Ung Joint Motion to Modify Scheduling Order, filed on Apr. 21, 2023, 1 page (Case 1:21-cv-10865-NMG, D149).

Milliman, Inc., Milliman Solutions, LLC, and Vigilytics LLC, Plaintiffs, vs. Gradient A.I. Corp., Stanford A. Smith, and Samuel Chase Pettus, Defendants. Plaintiff Vigilytics LLC's Unopposed Motion to Withdraw Joseph Dorris as Counsel, filed on Apr. 3, 2023, 4 pages (Case 1:21-cv-10865-NMG, D142).

Milliman, Inc., Milliman Solutions, LLC, and Vigilytics LLC, Plaintiffs, vs. Gradient A.I. Corp., Stanford A. Smith, and Samuel Chase Pettus, Defendants. Plaintiffs' Motion to Modify Scheduling Order to Extend Discovery, filed on Apr. 3, 2023, 12 pages (Case 1:21-cv-10865-NMG, D144).

Milliman, Inc., Milliman Solutions, LLC, and Vigilytics LLC, Plaintiffs, vs. Gradient A.I. Corp., Stanford A. Smith, and Samuel Chase Pettus, Defendants. Plaintiffs, ' Opposition to Defendants' Motion

(56) References Cited

OTHER PUBLICATIONS for Reconsideration, filed on Feb. 24, 2023, 12 pages (Civil Action No. 1:21-cv-10865-NMG, D137).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Plaintiffs' Responsive Claim Construction Brief, filed on Dec. 8, 2022, 29 pages (Case 1:21-cv-10865-NMG, D126).
*Milliman, Inc., Milliman Solutions, LLC, and Vigilytics LLC*, Plaintiffs, vs. *Gradient A.I. Corp., Stanford A. Smith, and Samuel Chase Pettus*, Defendants. Report on the Filing or Determination of an Action Regarding a Patent or Trademark, AO 120, filed on May 25, 2021, 2 pages (case 1:21-cv-10865-NMG,D2).
U.S. Appl. No. 61/222,428, filed Jul. 2, 2009, 27 pages.
Sweeney, "k-ANONYMITY: A Model for Protecting Privacy," International Journal of Uncertainty, Fuzziness and Knowledge-Based Systems, May 2002, 10(5);557-570.
U.S. Appl. No. 12/827,745, filed Jun. 30, 2010.
U.S. Appl. No. 14/732,358, filed Jun. 5, 2015.
U.S. Appl. No. 16/131,094, filed Sep. 14, 2018.
U.S. Appl. No. 14/082,433, filed Nov. 18, 2013.
U.S. Appl. No. 15/136,318, filed Apr. 22, 2016.
U.S. Appl. No. 15/606,265, filed May 26, 2017.
U.S. Appl. No. 15/939,727, filed Mar. 29, 2018.
U.S. Appl. No. 17/167,247, filed Feb. 4, 2021.
U.S. Appl. No. 60/154,726, Ober et al., filed Sep. 20, 1999.
U.S. Appl. No. 60/875,392, Kress et al., filed Dec. 18, 2006.
U.S. Appl. No. 61/222,428, Paris, III, filed Jul. 1, 2009.
Churches, "A proposed architecture and method of operation for improving the protection and privacy and confidentitality in diesease registers," BMC Medical Research Methodology, 2023, 3:(1)1-13.
*Milliman, Inc., Milliman Solutions, LLC, and Vigilytics LLC*, Plaintiffs, vs. *Gradient A.I. Corp., Standford A. Smith, and Samuel Chase Pettus*, Defendants. Certificate of Attorney Rachel E. Ellenberger, filed Aug. 4, 2023, 2 pages (case 1:21-cv-10865-NMG, D152-1)
*Milliman, Inc., Milliman Solutions, LLC, and Vigilytics LLC*, Plaintiffs, vs. *Gradient A.I. Corp., Standford A. Smith, and Samuel Chase Pettus*, Defendants. Motion for Admission Pro HAC Vice of Rachel E. Ellenberger, filed on Aug. 4, 2023, 2 pages (case 1:21-cv-10865-NMG, D152).
Uzuner et al. "Evaluating the State-of-the-Art in Automatic De-identification," J. Am. Med. Inform. Assoc., Oct. 2007, 14(5):550-563.
File History of U.S. Pat. No. 9,118,641, filed on Jun. 30, 2010, 468 pages (Exhibit 1002, IPR 2024-00226).
Declaration of Paul C. Clark, DSC. In Support of Petition for Inter Partes Review of U.S. Pat. No. 9,118,641, filed on Nov. 21, 2023, 110 pages (Exhibit 1003, IPR 2024-00226).
Curriculum Vitae of Dr. Paul Clark, filed on Nov. 22, 2023, 3 pages (Exhibit 1004, IPR 2024-00226)
Murphy, "A Security Architecture for Query Tools used to Access Large Biomedical Databases," 2002 AMIA Annual Sympossium Proceedings, AMIA 2002 Annual Symposium Proceedings, 552-556, 38 pages (Exhibit 1009, 2024-00226).
Hospitalityupgrade.com [online], "The Best Way to Secure Data Is Not to Store Data," Summer 2008, retrieved on Dec. 5, 2023, retrieved from URL<https://www.hospitalityupgrade.com/_magazine/magazine_Detail.asp/?ID=299>, 1 page (Exhibit 1011, IPR 2024-00226).
Steiner et al., "Kerberos: An Authentication Service for Open Network Systems," In Proceedings of the Winter 1988 Usenix Conference, Jan. 12, 1988, 15 pages (Exhibit 1012, IPR 2024-00226).
Declaration of Sylvia Hall-Ellis, Ph.d., IPR2024-00226 U.S. Pat. No. 9,118,641, filed on Nov. 21, 2023, 35 pages (Exhibit 1013, IPR 2024-00226).
*Datavant, Inc.*, Petitioner v. *Vigilytics LLC*, Patent Owner, IPR2024-00226, U.S. Pat. No. 9,118,641, Title: De-Identifying Medical History Information for Medical Underwriting, Petition for Inter Partes Review Under 35 U.S.C. §§ 311-319 and 37 C.F.R. §§ 42.100 et seq., filed on Nov. 22, 2023, 87 pages.

File History of U.S. Pat. No. 10,109,375, filed on Jun. 5, 2015, 326 pages (Exhibit 1002, IPR 2024-00311).
U.S. Pat. No. 10,109,375, issued on Oct. 23, 2018, 16 pages (Exhibit 1001, IPR 2024-00311).
U.S. Publ. No. 2007/029411, published on Dec. 20, 2007, 17 pages (Exhibit 1006, IPR 2024-00311).
U.S. Publ. No. US 2002/0111833, published on Aug. 15, 2002, 11 pages (Exhibit 1007, IPR 2024-00311).
U.S. Pat. No. 7,519,591, issued on Apr. 14, 2009, 13 pages (Exhibit 1008, IPR 2024-00311).
Declaration of Sylvia Hall-Ellis, Ph.D., filed on Dec. 15, 2023, 35 pages (Exhibit 1013, IPR2024-00311).
File History of U.S. Pat. No. 10,109,375, filed on Jun. 5, 2015, 216 pages (Exhibit 1002, IPR 2024-00311).
Steiner et al., "Kerberos: An Authenication Service for Open Network Systems," Jan. 12, 1988, 15 pages (Exhibit 1012, IPR2024-00311).
U.S. Pat. No. 9,965,651, issued on May 8, 2018, 16 pages (Exhibit 1001, IPR 2024-00311).
Curriculum Vitae of Dr. Pau; Clark, filed on Dec. 15, 2023, 3 pages (Exhibit 1004, IPR2024-00311).
Hospitalityupgrade.com [online], "The Best Way to Secure Data Is Not to Store Data," Summer 2008, retrieved on Dec. 5, 2023, retrieved from URL<https://www.hospitalityupgrade.com/_magazine/magazine_Detail.asp/?ID=299>, 1 page (Exhibit 1011, IPR 2024-00311).
Declaration of Dr. Paul Clark, filed on Dec. 15, 2023, 119 pages (Exhibit 1003, IPR2024-00311).
U.S. Pat. No. 7,823,207, published on Oct. 26, 2010, 19 pages (Exhibit 1005, IPR2024-00311).
*Milliman, Inc. v. Gradient A.I. Corp.*, No. 1:21-Cv-10865 (D. Mass.) Dkt. 108, filed on Oct. 20, 2022, 28 pages (Exhibit 1010, IPR2024-00311).
*Datavant, Inc.*, Petitioner v. *Vigilytics LLC*, Patent Owner, IPR2024-00311, U.S. Pat. No. 10,109,375, Title: De-Identifying Medical History Information for Medical Underwriting, Petition for Inter Partes Review Under 35 U.S.C. §§ 311-319 and 37 C.F.R. §§ 42.100 et seq., filed on Dec. 15, 2023, 87 pages.
Murphy, "A Security Architecture for Query Tools used to Access Large Biomedical Databases," 2002 AMIA Annual Symposium Proceedings, AMIA 2002 Annual Symposium Proceedings, 552-556, 38 pages (Exhibit 1009, IPR 2024-00311).
Declaration of Dr. Paul Clark, filed on Dec. 15, 2023, 111 pages (Exhibit 1003, IPR2024-00307).
Murphy, "A Security Architecture for Query Tools used to Access Large Biomedical Databases," 2002 AMIA Annual Symposium Proceedings, AMIA 2002 Annual Symposium Proceedings, 552-556, 38 pages (Exhibit 1009, IPR 2024-00307).
Steiner et al., "Kerberos: An Authentication Service for Open Network Systems," Jan. 12, 1988, 15 pages (Exhibit 1010, IPR2024-00307).
*Datavant, Inc.*, Petitioner v. *Vigilytics LLC*, Patent Owner, IPR2024-00307, U.S. Pat. No. 9,965,651, Title: De-Identifying Heathcare Data to Evaluate Post-Healthcare Facility Encounter Treatment Outcomes, Petition for Inter Partes Review Under 35 U.S.C. §§ 311-319 and 37 C.F.R. §§ 42.100 et seq., filed on Dec. 15, 2023, 90 pages.
U.S. Pat. No. 7,823,207, issued on Oct. 26, 2010, 19 pages (Exhibit 1005, IPR2024-00307).
U.S. Pat. No. 7,519,591, issued on Apr. 14, 2009, 13 pages (Exhibit 1008, IPR2024-00307).
Declaration of Sylvia Hall-Ellis, Ph.D., filed on Dec. 15, 2023, 35 pages (Exhibit 1013, IPR2024-00307).
U.S. Pat. No. 9,965,651, issued on May 8, 2018, 16 pages (Exhibit 1001, IPR2024-00307).
U.S. Publ. No. 2007/0294111, published on Dec. 20, 2007, 17 pages (Exhibit 1006, IPR2024-00307).
U.S. Publ. No. 2002/0111833, published on Aug. 15, 2002, 11 pages (Exhibit 1007, IPR2024-00307).
*Milliman, Inc. v. Gradient A.I. Corp.*, No. 1:21-Cv-10865 (D. Mass.) Dkt. 108, filed on Oct. 20, 2022, 28 pages (Exhibit 1010, IPR2024-00307).

(56) References Cited

OTHER PUBLICATIONS

File History of U.S. Pat. No. 9,965,651, filed on Jun. 5, 2015, 216 pages (Exhibit 1002 corrected, IPR2024-00307).
Curriculum Vitae of Dr. Paul Clark, filed on Dec. 15, 2023, 3 pages (Exhibit 1004, IPR2024-00307).
Hospitalityupgrade.com [online], "The Best Way to Secure Data Is Not to Store Data," Summer 2008, retrieved on Dec. 5, 2023, retrieved from URL<https://www.hospitalityupgrade.com/_magazine/magazine_Detail.asp/?ID=299>, 1 page (Exhibit 1011, IPR 2024-00307).
U.S. Publ. No. 2007/0294111, published on Dec. 20, 2007, 17 pages (Exhibit 1006, IPR2024-00381).
Murphy, "A Security Architecture for Query Tools used to Access Large Biomedical Databases," 2002 AMIA Annual Symposium Proceedings, AMIA 2002 Annual Symposium Proceedings, 552-556, 38 pages (Exhibit 1009, IPR 2024-00381).
U.S. Pat. No. 10,886,012, issued on Jan. 5, 2021, 15 pages (Exhibit 1001, IPR2024-00381).
Declaration of Dr. Paul Clark, filed on Jan. 4, 2024, 110 pages (Exhibit 1013, IPR2024-00381).
U.S. Pat. No. 7,519,591, issued on Apr. 14, 2009, 13 pages (Exhibit 1008, IPR2024-00381).
*Milliman, Inc. v. Gradient A.I. Corp.*, No. 1:21-Cv-10865 (D. Mass.) Dkt. 108, filed on Oct. 20, 2022, 28 pages (Exhibit 1010, IPR2024-00381).
Steiner et al., "Kerberos: An Authentication Service for Open Network Systems," Jan. 12, 1988, 15 pages (Exhibit 1012, IPR2024-00381).
*Datavant, Inc.*, Petitioner v. *Vigilytics LLC*, Patent Owner, IPR2024-00311, U.S. Pat. No. 10,886,012, Title: De-Identifying Medical History Information for Medical Underwriting, Petition for Inter Partes Review Under 35 U.S.C. §§ 311-319 and 37 C.F.R. §§ 42.100 et seq., filed on Jan. 4, 2024, 87 pages.
U.S. Pat. No. 7,823,207, issued on Oct. 26, 2010, 19 pages (Exhibit 1005, IPR2024-00381).
U.S. Publ. No. US 2002/0111833, published on Aug. 15, 2002, 11 pages (Exhibit 1007, IPR2024-00381).
Hospitalityupgrade.com [online], "The Best Way to Secure Data Is Not to Store Data," Summer 2008, retrieved on Dec. 5, 2023, retrieved from URL<https://www.hospitalityupgrade.com/_magazine/magazine_Detail.asp/?ID=299>, 1 page (Exhibit 1011, IPR 2024-00381).
Curriculum Vitae of Dr. Paul Clark, filed on Dec. 15, 2023, 3 pages (Exhibit 1004, IPR2024-00381).
Declaration of Sylvia Hall-Ellis, Ph.D., filed on Dec. 15, 2023, 35 pages (Exhibit 1013, IPR2024-00381).
File History of U.S. Pat. No. 10,866,012, filed on Sep. 14, 2018, 391 pages (Exhibit 1002, IPR2024-00381).
U.S. Pat. No. 9,965,651, issued on May 8, 2018, 16 pages (Exhibit 1001, IPR2024-00382).
*Milliman, Inc. v. Gradient A.I. Corp.*, No. 1:21-Cv-10865 (D. Mass.) Dkt. 108, filed on Oct. 20, 2022, 28 pages (Exhibit 1010, IPR2024-00382).
Declaration of Sylvia Hall-Ellis, Ph.D., filed on Jan. 4, 2024, 35 pages (Exhibit 1013, IPR2024-00382).
*Datavant, Inc.*, Petitioner v. *Vigilytics LLC*, Patent Owner, IPR2024-00382, U.S. Pat. No. 9,665,685, Title: Using De-Identified Healthcare Data to Evaluate Post-Healthcare Facility Encounter Treatment Outcomes, Petition for Inter Partes Review Under 35 U.S.C. §§ 311-319 and 37 C.F.R. §§ 42.100 et seq., filed on Jan. 4, 2024, 93 pages.
U.S. Publ. No. US 2002/0111833, published on Aug. 15, 2002, 11 pages (Exhibit 1007, IPR2024-00382).
U.S. Pat. No. 7,519,591, issued on Apr. 14, 2009, 13 pages (Exhibit 1008, IPR2024-00382).
Murphy, "A Security Architecture for Query Tools used to Access Large Biomedical Databases," 2002 AMIA Annual Symposium Proceedings, AMIA 2002 Annual Symposium Proceedings, 552-556, 38 pages (Exhibit 1009, IPR 2024-00382).
Hospitalityupgrade.com [online], "The Best Way to Secure Data Is Not to Store Data," Summer 2008, retrieved on Dec. 5, 2023, retrieved from URL<https://www.hospitalityupgrade.com/_magazine/magazine_Detail.asp/?ID=299>, 1 page (Exhibit 1011, IPR 2024-00382).
Steiner et al., "Kerberos: An Authentication Service for Open Network Systems," Jan. 12, 1988, 15 pages (Exhibit 1012, IPR2024-00382).
File History of U.S. Pat. No. 9,665,685, filed on Apr. 22, 2016, 221 pages (Exhibit 1002, IPR2024-00382).
U.S. Pat. No. 7,823,207, issued on Oct. 26, 2010, 19 pages (Exhibit 1005, IPR2024-00382).
U.S. Publ. No. US 2007/0294111, published on Dec. 20, 2007, 17 pages (Exhibit 1006, IPR2024-00382).
Declaration of Dr. Paul Clark, filed on Jan. 4, 2024, 108 pages (Exhibit 1013, IPR2024-00382).
Curriculum Vitae of Dr. Paul Clark, filed on Jan. 4, 2023, 3 pages (Exhibit 1004, IPR2024-00382).
*Milliman, Inc., Milliman Solutions, LLC, and Vigilytics LLC*, vs. *Gradient A.I. Corp., Standford A. Smith, and Samuel Chase Pettus*, Defendants. Joint Stipulation and Order of Dismissal with Prejudice, in The United States District Court of The District of Massachusentts, dated Apr. 19, 2024, 4 pages (Case 1:21-cv-10865-NMG, D248).
*Datavant, Inc.*, Petitioner v. *Vigilytics LLC*, Patent Owner, IPR2024-00311, U.S. Pat. No. 10,109,375, Decision Granting Institution of Inter Partes Review, dated Jun. 26, 2024, 42 pages.
*Datavant, Inc.*, Petitioner v. *Vigilytics LLC*, Patent Owner, IPR2024-00307, U.S. Pat. No. 9,965,651 B1, Decision Granting Institution of Inter Partes Review, dated Jun. 26, 2024, 40 pages.
*Datavant, Inc.*, Petitioner v. *Vigilytics LLC*, Patent Owner, IPR2024-00226, U.S. Pat. No. 9,118,641, Decision Granting Institution of Inter Partes Review, dated May 13, 2024, 26 pages.
*Datavant, Inc.*, Petitioner v. *Vigilytics LLC*, Patent Owner, IPR2024-00382, U.S. Pat. No. 9,665,685, Decision Granting Institution of Inter Partes Review, filed Jul. 12, 2024, 38 pages.
*Datavant, Inc.*, Petitioner v. *Vigilytics LLC*, Patent Owner, IPR2024-00381, U.S. Pat. No. 10,886,012, Decision Granting Institution of Inter Partes Review, filed Jul. 12, 2024, 56 pages.

\* cited by examiner

DE-IDENTIFYING MEDICAL HISTORY INFORMATION FOR MEDICAL UNDERWRITING

CLAIM OF PRIORITY

This application is a continuation application and claims priority under 35 USC § 120 to U.S. application Ser. No. 16/131,094, filed on Sep. 14, 2018, which is a continuation application of U.S. application Ser. No. 14/732,358, filed on Jun. 5, 2015 (now U.S. Pat. No. 10,109,375), which is a continuation application of U.S. application Ser. No. 12/827,745, filed on Jun. 30, 2010 (now U.S. Pat. No. 9,118,641), which claims benefit to U.S. Provisional Application Ser. No. 61/222,428, filed on Jul. 1, 2009, the entire contents of which are incorporated herein by reference.

BACKGROUND

The present disclosure relates to processing and transmitting personal data, the dissemination of which is restricted by federal law.

Due to federal privacy laws, companies that offer health insurance to small and midsize groups (containing 10-1000 individuals) are often unable to obtain the health history data they need to estimate the risk of insuring such groups commonly referred to as "experience rating". This frequently leads to less than optimal pricing for the companies, the groups, or both. Healthcare providers such as pharmacies and hospitals generate private healthcare data about patients, including medical and prescription drug history, and administrative healthcare claims data. Data that associates patient identity with health information is known as protected health information (PHI). Healthcare providers can store protected health information in electronic databases for future use in patient care and insurance claims processing. Insurance companies have developed techniques to estimate their risk from insuring a group of people by processing the protected health information about the group. Federal privacy laws, however, prevent the insurance companies from obtaining protected health information without individual authorizations from the each person in the group.

SUMMARY

The systems and techniques described here relate to de-identifying medical history information.

In one aspect, a computer-implemented method includes producing information that characterizes a group of individuals from a set of private data representing characteristics of the individuals. The identity of the individuals is unattainable from the produced information. The method also includes providing the produced information to report the characteristics of the group.

Implementations may include any of all of the following features. Producing information that characterizes the group may include producing a request token for each individual included in the group. Producing such a request token for each individual may include encrypting respective data that identifies each individual. Producing information that characterizes the group may include comparing the request tokens to tokens associated with the information to be produced. The tokens associated with the information to be produced and the request tokens may be similarly encrypted. Producing information that characterizes the group may includes determining if the comparison provides at least a minimum number of matches. Producing information that characterizes the group may include requesting a predefined portion of the information. Additionally, producing information that characterizes the group may include determining if the group includes at least a minimum number of individuals. The private data may represent medical related information associated with the individuals of the group.

In another aspect a system includes an encryption server for producing a request token of each individual included in a group identified in a request for information that characterizes the group. The system may also include a data server for producing the information that characterizes the group from a set of private data representing characteristics of the individuals. The identity of the individuals is unattainable from the produced information. The data server is also configured to provide the produced information to report the characteristics of the group.

Implementations may include any of all of the following features. The data server may provide a request token for each individual included in the group to produce the information that characterizes the group. The request token for each individual may represent encrypted data that identifies the corresponding individual. The data server may be configured to compare the request tokens to tokens associated with the information to be produced. The tokens associated with the information to be produced and the request tokens may be similarly encrypted. The data server may be configured to determine if the comparison provides at least a minimum number of matches. The request may represent a predefined portion of information to use for producing the information that characterizes the group. The encryption server may be configured to determine if the group includes at least a minimum number of individuals. The private data may represent medical related information associated with the individuals of the group.

In another aspect, one or more computer readable media storing instructions that are executable by a processing device, and upon such execution cause the processing device to perform operations that include producing information that characterizes a group of individuals from a set of private data representing characteristics of the individuals. The identity of the individuals is unattainable from the produced information. The operations also include providing the produced information to report the characteristics of the group.

Implementations may include any of all of the following features. Producing information that characterizes the group may include producing a request token for each individual included in the group. Producing such a request token for each individual may include encrypting respective data that identifies each individual. Producing information that characterizes the group may include comparing the request tokens to tokens associated with the information to be produced. The tokens associated with the information to be produced and the request tokens may be similarly encrypted. Producing information that characterizes the group may includes determining if the comparison provides at least a minimum number of matches. Producing information that characterizes the group may include requesting a predefined portion of the information. Additionally, producing information that characterizes the group may include determining if the group includes at least a minimum number of individuals. The private data may represent medical related information associated with the individuals of the group.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
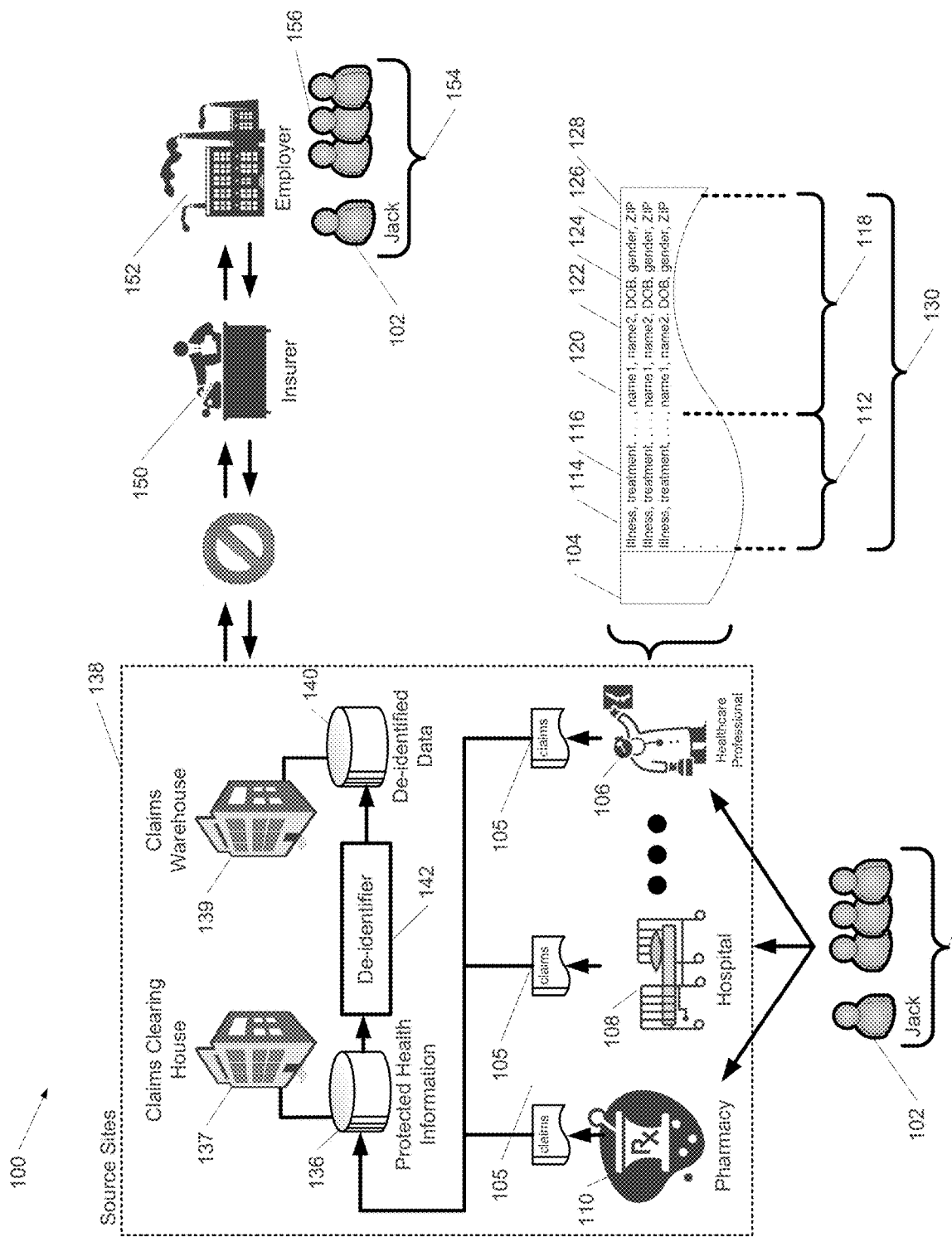
FIG. 1 illustrates exemplary circumstances in which protected health information is stored by healthcare providers, claims clearing houses, and other source sites, and requested by an insurer.

Referring to FIG. 1, when a doctor treats Jack 102 for high blood pressure, a surgeon removes Jack's gallstones, and a pharmacist fills Jack's prescription for insulin, Jack leaves a trail of electronic records 104 with healthcare professionals (e.g., healthcare profession 106), in their offices (e.g., doctor's office, nurse's station, etc.), in healthcare facilities (e.g., a hospital 108, a pharmacy 110, a nursing home, etc.) and the like. The electronic records 104 contain medical data 112 about Jack, for example his illnesses 114 and treatments 116. Each piece of medical data 112 is associated with personally identifiable information 118 that identifies Jack and distinguishes him from all other patients, such as his first name 120, last name 122, date of birth 124, gender 126, and zip code 128. Together, the pieces of medical data 112 and the personally identifiable information 118 make up Jack's protected health information (PHI) 130.

Each of Jack's healthcare providers may submit health insurance claims 105 containing PHI 130, as well as additional PHI 130, to a claims clearing house 137. The claims clearing house 137 may store the PHI 130 of many patients 134, including Jack, in a PHI database 136. A de-identifier 142 can process the PHI 136 to generate irreversibly de-identified data 140 by removing all personally identifiable information 118 or otherwise transforming the PHI 130 so that it cannot be associated with a particular person. A claims warehouse 139 stores de-identified data 140 about many patients 134. Claims clearing houses 137 and claims warehouses 139 are optimized for retrieving and providing PHI 136 and de-identified data 140 for use in further processing, but health care providers such as healthcare professional 106 and pharmacies 110 may also serve as source sites 138 for de-identified data in a distributed system.

By searching for Jack's personally identifiable information 118 in its electronic records 104, the pharmacy 110 is able to look up the various drugs in Jack's PHI 130 and, for example, check for bad interactions among them. Jack does not object to this use of his PHI 130 because it improves the quality of his healthcare. On the other hand, Jack would object to the pharmacy 110 giving his PHI 130 to third parties without his permission because that would disclose personal, private information about him that Jack's potential employers, for example, might use to discriminate against him.

Federal laws, such as the Health Insurance Portability and Accountability Act (HIPAA), protect Jack by prohibiting the source sites 138 possessing Jack's PHI 130 from releasing it to third parties without Jack's permission. Under HIPAA, the source sites 138 can release only irreversibly de-identified data 140 without Jack's permission.

A health insurer 150, for example, may be interested in the medical history information contained in Jack's PHI 130. Jack's employer 152 may like to buy a group health insurance policy for the group 154 made up of Jack 102 and his coworkers 156. If the group 154 is too small, the insurance company 150 will not have the knowledge to fully understand the potential risk from future medical claims for the group 154 and need to set the rate to cover this unknown risk. In that case, the insurer 150 would like to use the PHI 136 from the group 154 to assess the risk of claims and set the group health insurance premium appropriately. Unfortunately, the group 154 may also be too large for the insurance company 150 to practically obtain permission from each person in the group, without which HIPAA prohibits the healthcare providers 138 from releasing the PHI 136 to the insurer 150. The de-identified data 140, which the healthcare providers or other source sites 138 could release without permission, is not useful to the insurer 150 because the insurer has no way to know whether it corresponds to the people in the group 154. With no way to obtain medical history data for the group, the insurer 150 cannot set the group insurance premium acceptably.

Figure 2:
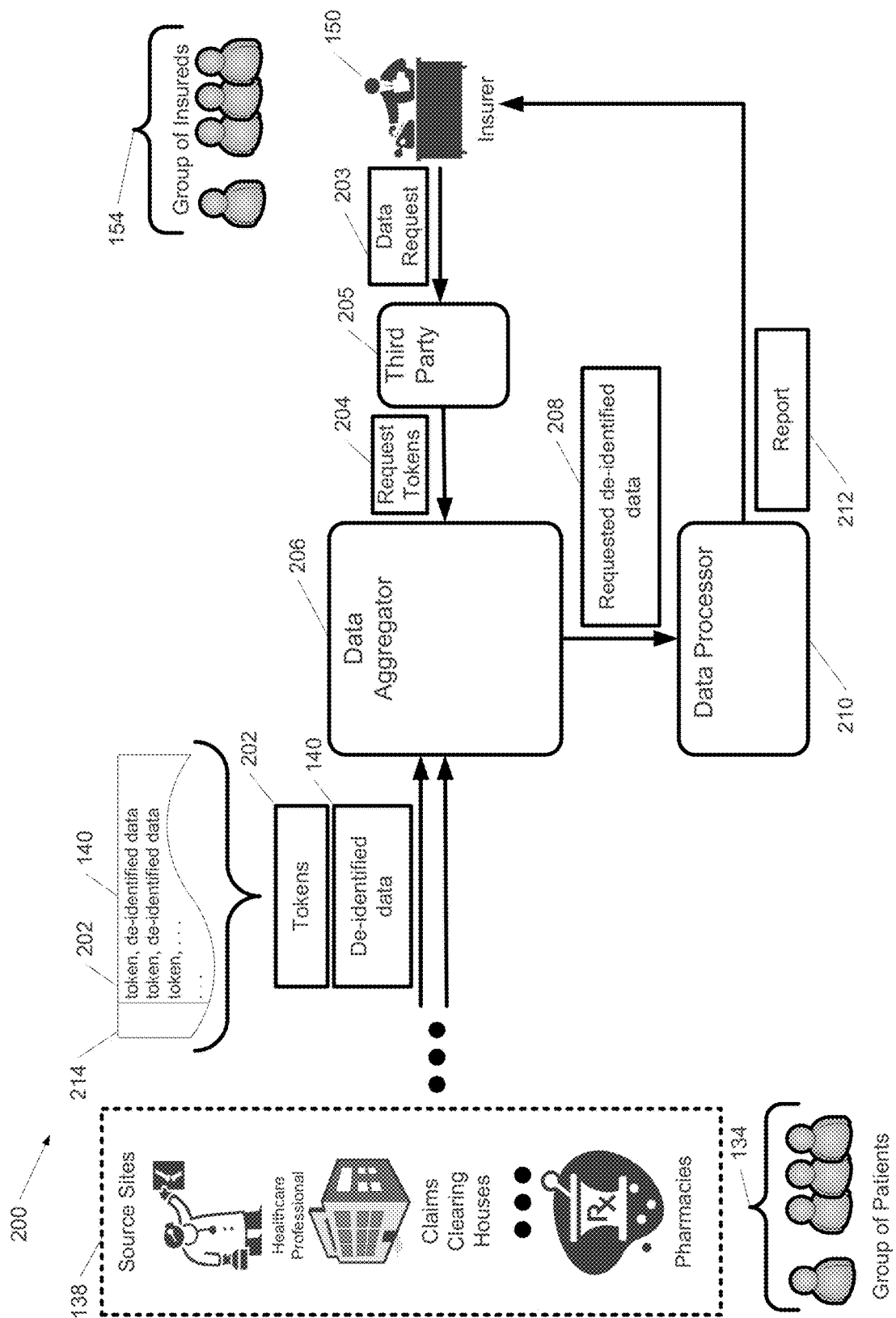
FIG. 2 illustrates an exemplary method and system that enables an insurer to obtain medical information about a group of people without violating the privacy of persons in the group.

Referring to FIG. 2, to provide the insurer 150 with the medical history information necessary to calculate the insurance premium for the group 154, without revealing the protected health information of persons in the group 154, the exemplary system 200 associates unique tokens 202 with the irreversibly de-identified data 140. The tokens 202 correspond to persons treated by healthcare providers but do not reveal the identities of the treated individuals. The insurer 150 can send a data request 203 to a third party 205, who in turn can generate request tokens 204, one for each person in the group 154. The third party 205 can send the request tokens 204 to a data aggregator 206. The data aggregator 206 stores de-identified data 140 and associated tokens 202. By searching for the request tokens 204 among the stored tokens 202, the data aggregator 206 can process the de-identified data to generate requested de-identified data 208 that corresponds to the group 154. A data processor 210 can process the requested de-identified data 208 to generate a report 212 containing metrics such as underwriting scores that are useful to the insurer 150 in assessing the overall risk of insuring the group 154.

By using the tokens 202 and request tokens 204, no parties other than the authorized source sites 138 can associate de-identified data 140 with the identity of any person in the group of patients 134 or insureds (e.g., the group 154). The insurer 150 requesting the report 212 can never receive data associated with individuals. Further, the information in the report 212 may be processed into metrics that characterize a large group and cannot be used to infer information about individuals. De-identified data records may be provided to the data processor 210 (e.g., a third part data processor), but that third party may not have access to any personally identifiable information 118 about the group 154. Nor may any party with access to the de-identified data 140, other than the healthcare providers 138, also have access to the de-identifier 142. These features of the system 200 maintain the privacy of the protected health information 130.

While we describe a system in which an insurer 150 needs to estimate the risk of insuring a group of potential customers, the system 200 can work for applications in which information characterizing a group needs to be generated from the private data of group members. In one arrangement, the system may implement Microsoft Windows-based computers in connection with internet-based components. However, other implementations may use other types of components that support the processing of medical history information from healthcare databases.

Figure 3:
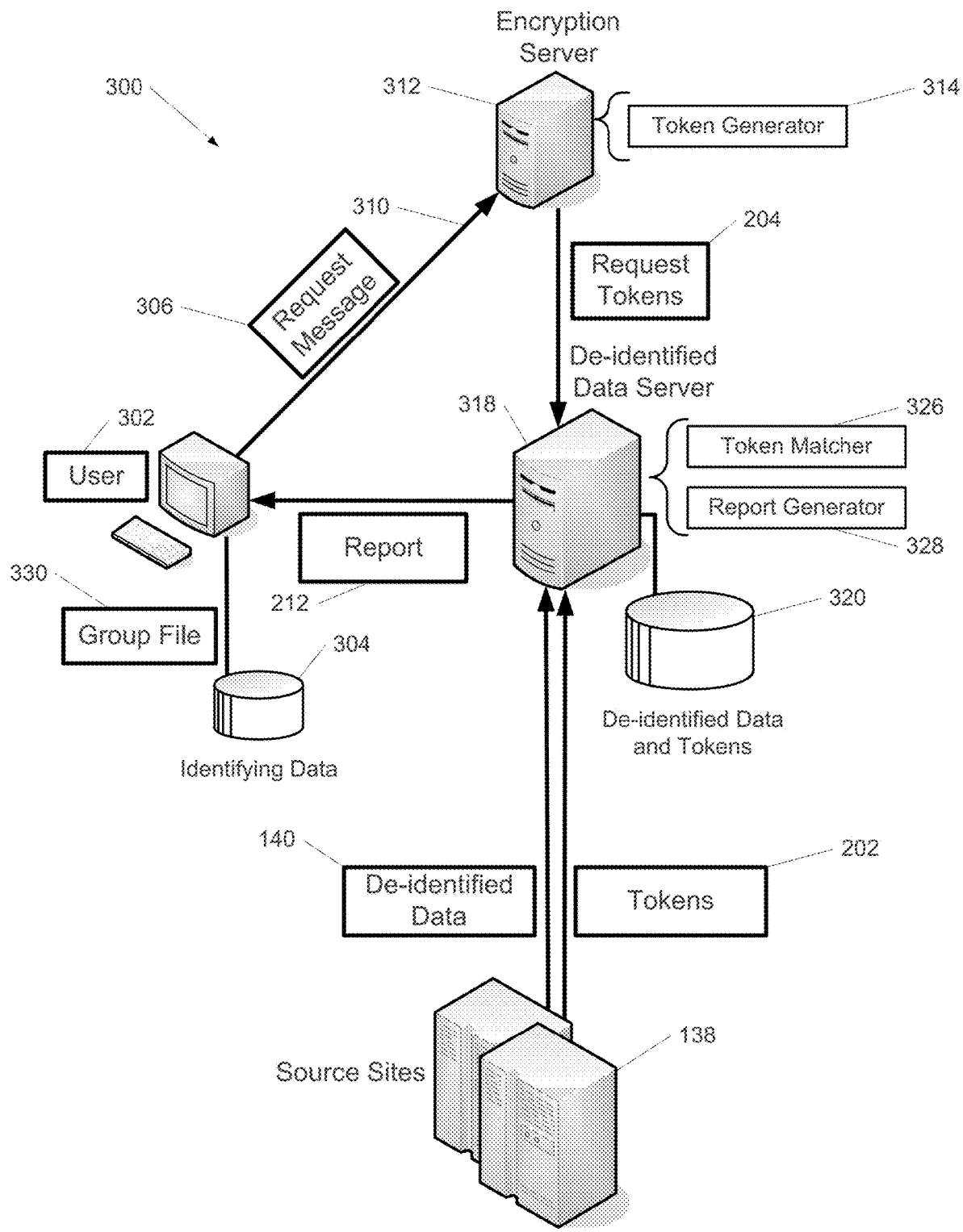
FIG. 3 illustrates an exemplary system incorporating an encryption server and a de-identified data server to enable a user who is not permitted to obtain the private data of a group of people to instead obtain a report that characterizes the group as a whole.
Figure 4:
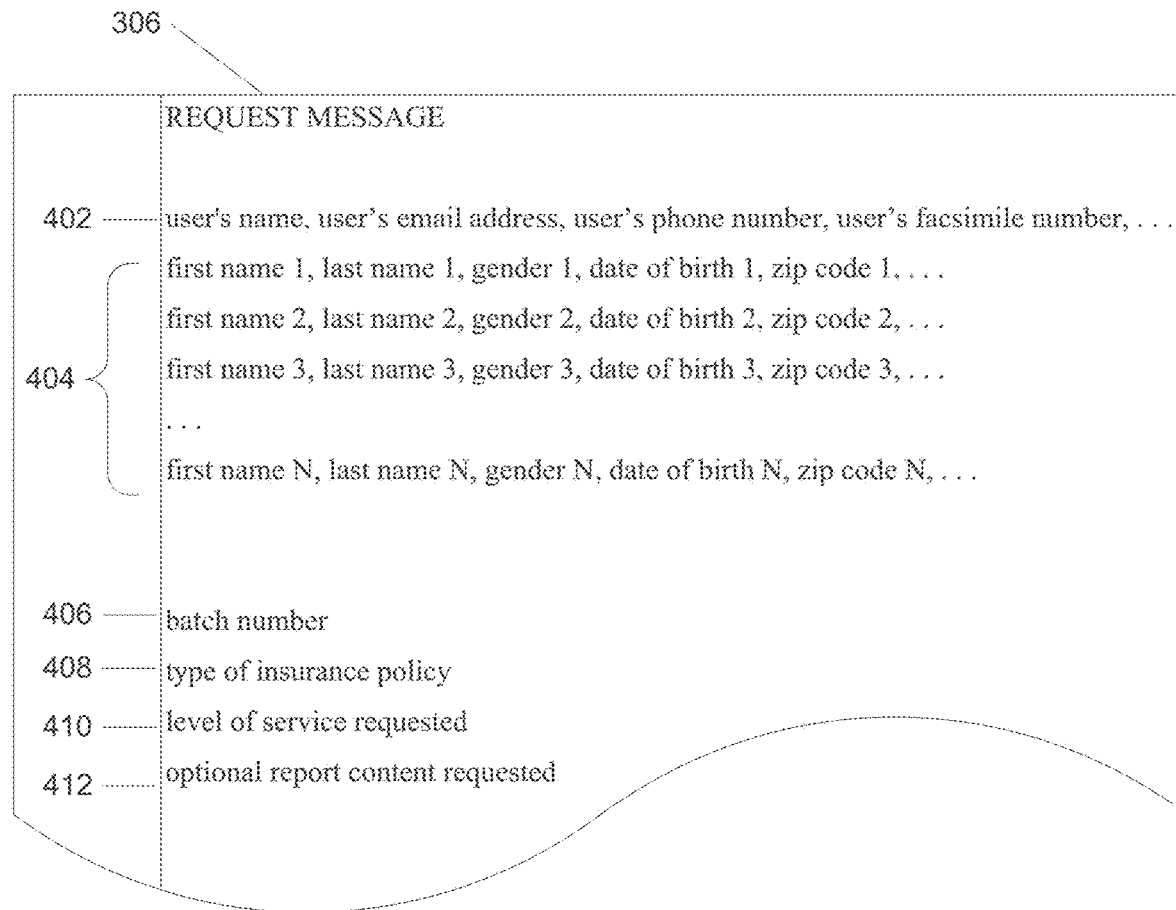
FIG. 4 illustrates an exemplary message requesting de-identified data about a group of people.

Referring to FIG. 3, in an exemplary system 300, a user 302 specifies a group of people using identifying data for each group member. Referring briefly to FIG. 4, an exemplary set of identifying data 404 is illustrated. Returning to FIG. 3, the user may obtain the personally identifiable information from a database 304 by retrieving it in the form of a group file 330. The user 302 generates a request message, which may be a computer file, which uniquely identifies each member of the group using the identifying data 304. Typically, the group contains at least a minimum number of unique members. A request message 306 may be generated at a remote computer operated by the user 302.

The request message 306 contains a set of identifying data 404 (see FIG. 4) for each group member, as well as data that identifies a user 402 (see FIG. 4), such as the user's name, email address, phone number and facsimile number, and a batch number that identifies the request. The group members' identifying data 404 (see FIG. 4) may include first name, last name, date of birth, gender, and zip code as well as other identifiers, such as social security number, that may be added to ensure that members are uniquely identified. In some examples, fewer identifiers may be used. The request message 306 may also include optional indications that the user 302 requests a particular type of report 212 or requests additional processing to enhance the value of the report.

The request message 306 is sent over a communications network 310 (e.g., the Internet, a LAN, etc.) to an encryption server 312. If the request message 306 contains a minimum number of group members, the encryption server 312 creates a unique token, or identifier, for each person in the message 306. The encryption server creates each token by applying a token generator 314 that encrypts the personally identifiable information of each group member. The set of tokens corresponding to all the group members constitutes a batch of request tokens 204. The minimum number of group members, for example ten, is chosen to make it effectively impossible to associate individual group members with individual tokens in the batch of request tokens 204.

The encryption server 312 provides the request tokens 204 to the de-identified data server 318. The de-identified data server 318 stores records of de-identified data and corresponding tokens 320 obtained from source sites 138 such as pharmacies, healthcare professionals and electronic claims clearing houses. Each token obtained from the source sites 138 may have been created using the same token generator 314 used by the encryption server 312, or using any other means that generates the identical token for the same personally identifiable information.

For example, a pharmacy tracks the prescription histories of the patients being served. De-identified prescription histories and corresponding tokens are sent to the de-identified data server 318. At the request of a user 302, such as an insurance company, the encryption server 312 generates tokens identical to the patients' tokens using the same personally identifiable information. A unique token corresponding to the same personally identifiable information permits the pharmacy and the insurance company to refer to the same anonymous people without the insurance company ever associating protected health information with a particular person. To produce tokens and request tokens, one or more encryption techniques may be utilized, for example, hash functions and other methodologies may be implemented.

A token matcher 326, executed by the de-identified data server 318, performs a look-up in the de-identified database 320 to find all tokens in the database that match the tokens sent from the encryption server 312. All available data for matched tokens, the requested de-identified data 208, is retrieved for use in the report generator 328. The de-identified data may include, for example, prescription history, medical claims, and hospital claims. The de-identified data server 318, or the data processor 210 may use the report generator 328 to process the requested de-identified data 208 in a way that leaves it irreversibly de-identified. An example of such processing is an underwriting algorithm that transforms the data into an underwriting assessment. The report generator formats the processed data into an electronic or hardcopy report 212 that is returned to the user.

While the report 212 is described as generated on a computer system, it may also be generated in part or entirely outside the computer system. For example, the report 212 could be conveyed to the user via regular mail or other similar technique. In particular, the report may be generated and printed at the site of the de-identified data server 318 and subsequently communicated to the user 302 without using the computer network. The report generator 328 may also reside in the data processor 210 separate from the de-identified data server 318.

In one arrangement, once the relevant information and options have been selected, the user 302 submits the request by clicking a submit button. The request message 306 may be encrypted prior to being transmitted over a computer network 310. At the encryption server 312, the request message 306 is unencrypted and stored. The encryption server 312 may send an optional confirmation message to the user 302. The confirmation message may include the time and date that the message was received, and may indicate the service level and options selected by the user 302.

Referring to FIG. 4, the user 302 can input the user's identifying information 402, including name, email address, phone number and/or facsimile number, in the first record, or set of fields, of the request message 306. The user can then input the personally identifiable information 404 for each of the group members, including first name, last name, gender, date of birth, and zip code. Equivalently, the user can incorporate the group file 330 into the request message 306. Information about the insurance policy 408 for which the group has applied, or other insurance purpose for which the report 212 is being requested may also be included in the request message 306. The format of the request message 306 may be adjusted based on the user's 302 needs.

The request message 306 may also include information about the level of service 410 requested by the user 302, for example the quantity, quality or type of information. A first level of service may request up to six months of medical history; a second level may request up to twelve months of history; and a third level may request a two year medical history. Alternatively, instead of providing the user 302 with a variety of service level options 410, the system 300 may simply retrieve all of the medical history information available for the group.

The user 302 may also request additional, optional information 412. For example, the user 302 may request information regarding the drug categories and drug indications associated with the drugs in the de-identified data. Drug indications include the medical conditions associated with each drug. Drug categories include the type of drug. This data can be passed to the data processor 210 to include in the report 212. Alternatively, this data may be returned as part of every report 212.

Figure 5:
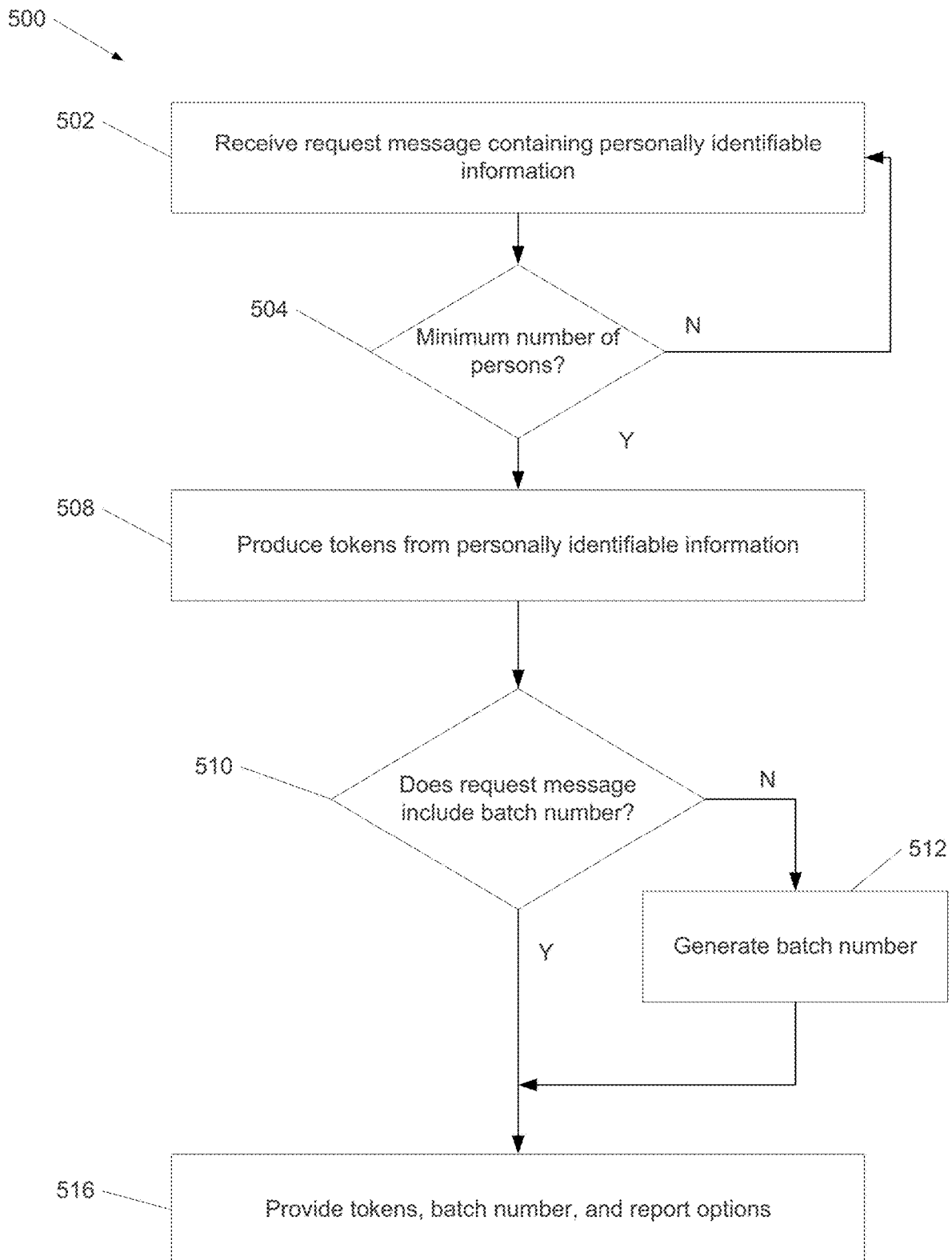
FIG. 5 is a flowchart that represents exemplary operations of a token generator.

Referring to FIG. 5, a flowchart 500 represents a particular arrangement of operations of a token generator (e.g., the token generator 314 shown in FIG. 3). Operations include receiving 502 the request message (e.g., request message 306) containing the personally identifiable information of each person in the group (e.g., such as the group 154 shown in FIG. 1). Upon receiving the request message, operations may also include determining 504 whether the message includes the minimum number of persons. If the message does not include the minimum number of persons, the token generator returns to receive 502 a request message. A limit on the minimum number of persons ensures that a report (e.g., the report 212) covers enough people such that it is difficult (if not impossible) to infer any association between particular persons and the information in the report. If the message does include the minimum number of people, operations of the token generator include producing 508 tokens from the identifying data of each person. Producing the tokens may include applying an encryption algorithm to the identifying data of each person. The tokens uniquely identify each person in the group 154.

Operations also include determining 510 if the request message includes a batch number. If the message does not include a batch number, operations include generating 512 a batch number. Operations also include providing 516 the tokens, batch number and report options. The individual tokens are placed in a batch file and may be encrypted before being transmitted over the network.

Each batch file of request tokens 204 also specifies the information needed for the report 212. The request tokens are transmitted to the de-identified data server 318, unencrypted and processed using rules for searching, matching, and retrieving healthcare data.

Figure 6:
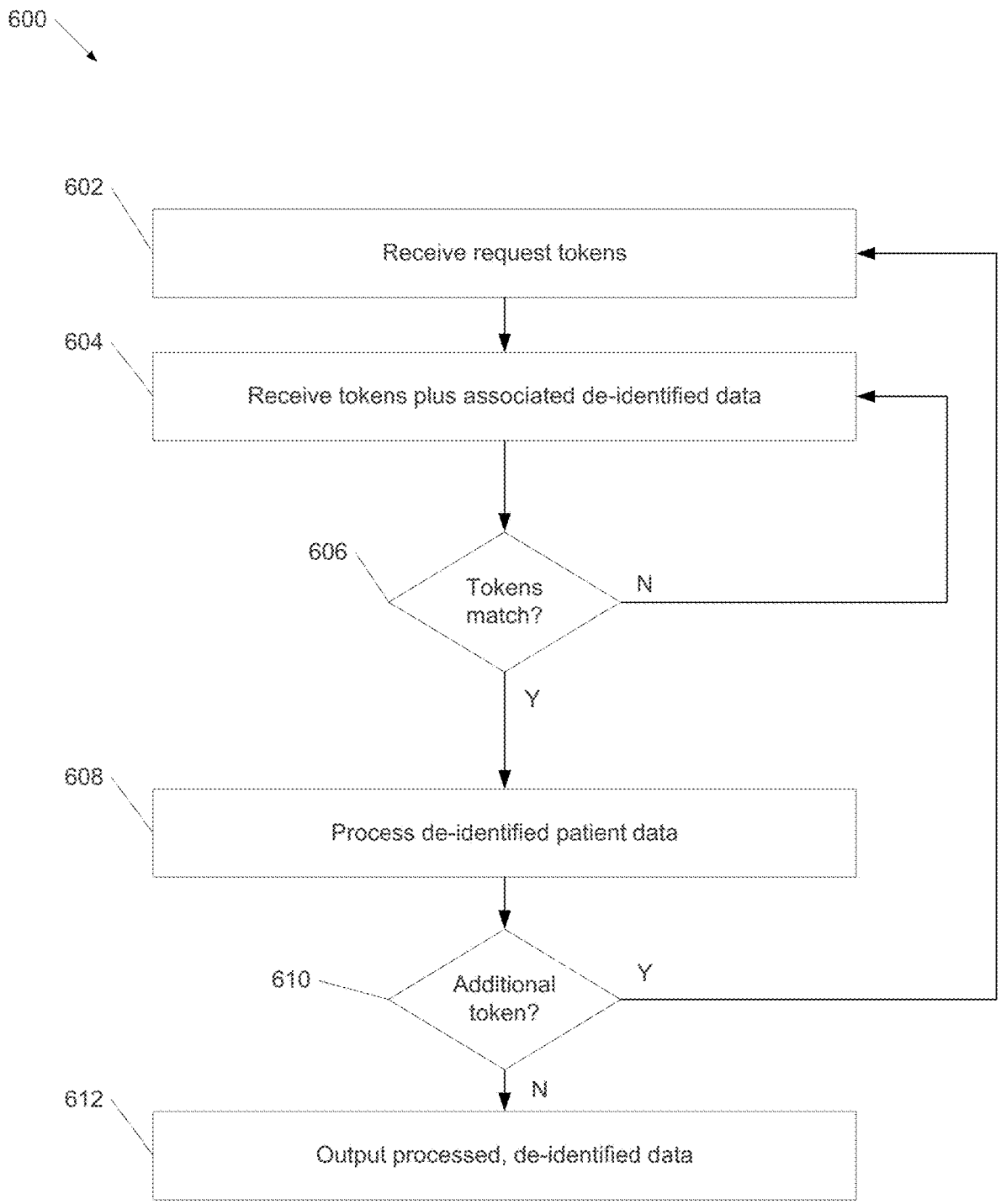
FIG. 6 is a flowchart that represents exemplary operations of a token matcher.

Referring to FIG. 6, a flowchart 600 represents a particular arrangement of operations of a token matcher (e.g., the token matcher 326 shown in FIG. 3). Operations include receiving 602 request tokens (e.g., such as the request tokens 204 shown in FIG. 2). Operations may also include receiving 604 a token (e.g., such as the token 202) and associated de-identified data (e.g., such as the de-identified data 140), typically from source sites (e.g., such as the source site 138 shown in FIG. 1). Upon receiving a request token, de-identified data and a token, operations include determining 606 whether the request token matches the token. If no match is found, operations include returning to receive 604 more tokens and de-identified data. If a match is found, operations include processing 608 the de-identified data. Processing may include storage for later retrieval. In some arrangements, operations may also include determining whether a minimum number of matches has been detected. If such a minimum number of matches has not occurred in comparing the request tokens and the tokens, action may be taken (e.g., pause or restart processing) until the predefined number of matches has been detected (e.g., so as not to increase the probability of one or more individuals being identified by a process of elimination).

The de-identified data (e.g., such as the de-identified data 140) may include a list of drugs prescribed over the requested period for the members of the group (e.g., such as the group 154). The list of drugs prescribed may include the drug name, form, strength, days supplied, and date dispensed. As part of processing 608 the de-identified data, operations may include determining the drug category and drug indications for each drug prescribed. Operations may also include accessing a database relating the drug category and indications to each possible drug. The database may be maintained within the de-identified data server 318 database, or may be accessed on a remote server maintained by a third party.

Upon processing the de-identified data, operations also include determining 610 if additional tokens remain in the batch of request tokens (e.g., such as the request tokens 204). If additional tokens remain, operations include receiving 602 more request tokens. If there are no additional request tokens, operations may include outputting 612 the processed, de-identified data.

Operations may also include providing the number of tokens submitted, the number matched, and the overall match rate. The collected data covers the interval of historical data according to the level of service requested (e.g., as represented by the level of service 410 in FIG. 4). De-identified diagnosis and procedures data may also be included from administrative medical claims from a doctor's office (e.g., office 106) or a healthcare facility (e.g., the hospital 108).

In addition to accessing and incorporating drug indication information for each drug prescribed to persons in the group (e.g., such as group 154), operations may include further processing of the requested de-identified data. For instance, operations may include determining the probability that a particular drug indicates a particular condition. In this example, in addition to providing the possible indications, the requested de-identified data would include the likelihood that anonymous individuals associated with the request tokens (e.g., such as request tokens 204) have each of the conditions indicated by the prescribed drugs. Operations may also include using expert rule systems to provide health status information based on the prescription drug history information. Alternatively, operations may include using diagnosis codes from medical claims data to assess health status.

The requested de-identified data 208 may be sent for further processing to a third party data processor (e.g., data processor 210) who may apply proprietary algorithms, modify the data format, or generate additional reports, provided that no re-identifiable information is transmitted to the user 302. Third parties may not have access to the request message 306 and the group file 330 so that no association may be inferred between the de-identified data 140 and particular persons in the group 154.

The report 212 provides the insurer 150 with information for making an immediate, informed decision about the insurance related risks. In particular, the insurer 150 may accept, reject or adjust the group's insurance rating depending on the information in the report 212. Actuarial tables and formulas may be used to determine which of the insurance actions are taken. The report 212 may be used alone to make decisions about the insurability of the group 154, or may simply indicate that additional investigation is needed.

Figure 7:
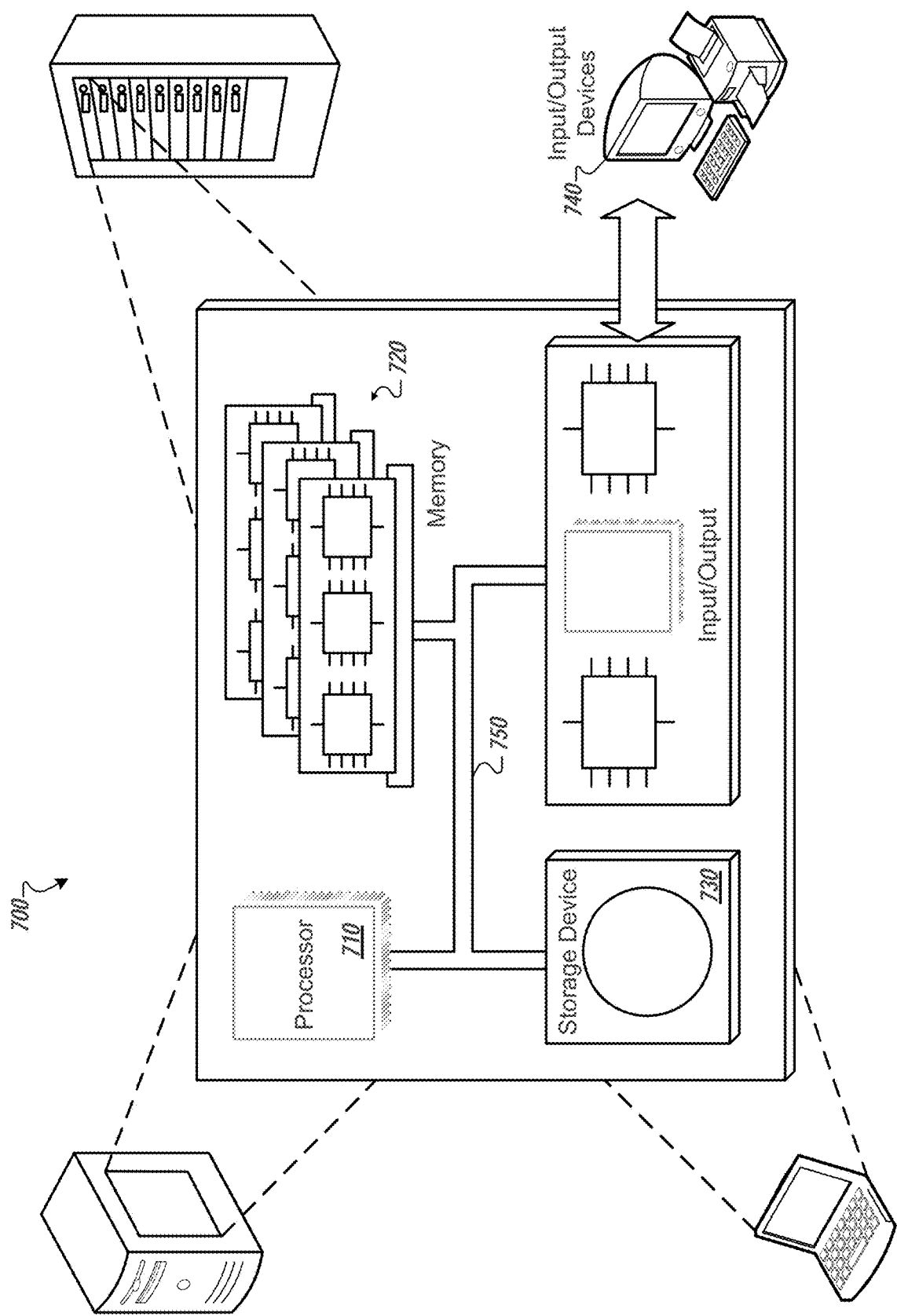
FIG. 7 represents a computer system and related components.

FIG. 7 is a schematic diagram of a generic computer system 700. The system 700 can be used for the operations described in association with any of the computer-implemented methods described previously, according to one implementation. The system 700 includes a processor 710, a memory 720, a storage device 730, and an input/output device 740. Each of the components 710, 720, 730, and 740 are interconnected using a system bus 750. The processor 710 is capable of processing instructions for execution within the system 700. In one implementation, the processor 710 is a single-threaded processor. In another implementation, the processor 710 is a multi-threaded processor. The processor 710 is capable of processing instructions stored in the memory 720 or on the storage device 730 to display graphical information for a user interface on the input/output device 740.

The memory 720 stores information within the system 700. In some implementations, the memory 720 is a computer-readable medium. The memory 720 is a volatile memory unit in some implementations and is a non-volatile memory unit in other implementations.

The storage device 730 is capable of providing mass storage for the system 700. In one implementation, the storage device 730 is a computer-readable medium. In various different implementations, the storage device 730 may be a floppy disk device, a hard disk device, an optical disk device, or a tape device.

The input/output device 740 provides input/output operations for the system 700. In one implementation, the input/output device 740 includes a keyboard and/or pointing device. In another implementation, the input/output device 740 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

A number of implementations have been described. Nevertheless, it will be understood that various modifications may be made without departing from the spirit and scope of the following claims.

What is claimed is:

1. A computer-implemented method comprising:
    receiving, at an encryption server, a request from a user device for healthcare information that characterizes a first group composed of multiple individuals, wherein at least one of the multiple individuals has not authorized provision of personal healthcare information at any time;
    determining that the first group comprises at least a defined minimum number of individuals;
    subsequent to determining that the first group comprises at least the defined minimum number of individuals, producing, by a processor of the encryption server, one or more request tokens from a first set of personally identifiable information associated with the multiple individuals, wherein the first set of personally identifiable information is provided in the request and wherein each of the one or more request tokens is unique to a corresponding individual of the multiple individuals;
    comparing the request tokens to tokens generated independently of the request tokens to find matching tokens,
    wherein the independently generated tokens are generated from a second set of personally identifiable information associated with a second group of individuals, each of the independently generated tokens being unique to a corresponding individual from the second group and associated with de-identified healthcare information about the corresponding individual from the second group, and wherein at least a portion of the independently generated tokens match at least a portion of the request tokens if the portion of the independently generated tokens and the portion of the request tokens correspond to the same individuals;

producing the de-identified healthcare information associated with the independently generated tokens that were matched to the request tokens; and providing the produced de-identified healthcare information to report characteristics of the first group.

2. The computer-implemented method of claim 1, wherein the provided de-identified healthcare information is provided in conformity with the Health Insurance Portability and Accountability Act (HIPAA).

3. The computer-implemented method of claim 1, in which producing the one or more request tokens includes encrypting at least a portion of the first set of personally identifiable information associated with the multiple individuals.

4. The computer-implemented method of claim 1, in which the independently generated tokens and the request tokens are similarly encrypted.

5. The computer-implemented method of claim 1, in which the healthcare information that characterizes the first group of multiple individuals represents medical related information associated with the multiple individuals of the first group.

6. The computer-implemented method of claim 1, wherein producing the one or more request tokens comprises producing the one or more request tokens in a reproducible manner.

7. A system comprising:
one or more computing devices comprising:
a memory configured to store instructions; and
a processor to execute the instructions to perform operations comprising:
receiving a request from a user device for healthcare information that characterizes a first group composed of multiple individuals, wherein at least one of the multiple individuals has not authorized provision of personal healthcare information at any time;
determining that the first group comprises at least a defined minimum number of individuals;
subsequent to determining that the first group comprises at least the defined minimum number of individuals, producing one or more request tokens from a first set of personally identifiable information associated with the multiple individuals, wherein the first set of personally identifiable information is provided in the request and wherein each of the one or more request tokens is unique to a corresponding individual of the multiple individuals;
comparing the request tokens to tokens generated independently of the request tokens to find matching tokens,
wherein the independently generated tokens are generated from a second set of personally identifiable information associated with a second group of individuals, each of the independently generated tokens being unique to a corresponding individual from the second group and associated with de-identified healthcare information about the corresponding individual from the second group, and wherein at least a portion of the independently generated tokens match at least a portion of the request tokens if the portion of the independently generated tokens and the portion of the request tokens correspond to the same individuals;

producing the de-identified healthcare information associated with the independently generated tokens that were matched to the request tokens; and providing the produced de-identified healthcare information to report characteristics of the first group.

8. The system of claim 7, wherein the provided de-identified healthcare information is provided in conformity with the Health Insurance Portability and Accountability Act (HIPAA).

9. The system of claim 7, in which producing the one or more request tokens includes encrypting at least a portion of the first set of personally identifiable information associated with the multiple individuals.

10. The system of claim 7, in which the independently generated tokens and the request tokens are similarly encrypted.

11. The system of claim 7, in which the healthcare information that characterizes the first group of multiple individuals represents medical related information associated with the multiple individuals of the first group.

12. The system of claim 7, wherein producing the one or more request tokens comprises producing the one or more request tokens in a reproducible manner.

13. One or more computer readable storage devices storing instructions that are executable by a processing device, and upon such execution cause the processing device to perform operations comprising:
receiving, at an encryption server, a request from a user device for healthcare information that characterizes a first group composed of multiple individuals, wherein at least one of the multiple individuals has not authorized provision of personal healthcare information at any time;
determining that the first group comprises at least a defined minimum number of individuals;
subsequent to determining that the first group comprises at least the defined minimum number of individuals, producing, by a processor of the encryption server, one or more request tokens from a first set of personally identifiable information associated with the multiple individuals, wherein the first set of personally identifiable information is provided in the request and wherein each of the one or more request tokens is unique to a corresponding individual of the multiple individuals;
comparing the request tokens to tokens generated independently of the request tokens to find matching tokens,
wherein the independently generated tokens are generated from a second set of personally identifiable information associated with a second group of individuals, each of the independently generated tokens being unique to a corresponding individual from the second group and associated with de-identified healthcare information about the corresponding individual from the second group, and wherein at least a portion of the independently generated tokens match at least a portion of the request tokens if the portion of the independently generated tokens and the portion of the request tokens correspond to the same individuals;

producing the de-identified healthcare information associated with the independently generated tokens that were matched to the request tokens; and providing the produced de-identified healthcare information to report characteristics of the first group.

14. The computer readable storage devices of claim 13, wherein the provided de-identified healthcare information is provided in conformity with the Health Insurance Portability and Accountability Act (HIPAA).

15. The computer readable storage devices of claim 13, in which producing the one or more request tokens includes encrypting at least a portion of the first set of personally identifiable information associated with the multiple individuals.

16. The computer readable storage devices of claim 13, in which the independently generated tokens and the request tokens are similarly encrypted.

17. The computer readable storage devices of claim 13, in which the healthcare information that characterizes the first group of multiple individuals represents medical related information associated with the multiple individuals of the first group.

18. The computer readable storage devices of claim 13, wherein producing the one or more request tokens comprises producing the one or more request tokens in a reproducible manner.

* * * * *